(12) United States Patent
Bansal

(10) Patent No.: US 9,023,831 B2
(45) Date of Patent: May 5, 2015

(54) METHODS AND COMPOSITIONS OF INHIBITING COMPLEMENT AND CELLULAR ACTIVATION WITH DEXTRAN SULFATE

(75) Inventor: Rekha Bansal, Twinsburg, OH (US)

(73) Assignee: Novelmed Therapeutics, Inc., Cleveland, OH (US)

( * ) Notice: Subject to any disclaimer, the term of this patent is extended or adjusted under 35 U.S.C. 154(b) by 424 days.

(21) Appl. No.: 12/597,321

(22) PCT Filed: Apr. 24, 2008

(86) PCT No.: PCT/US2008/061423
§ 371 (c)(1),
(2), (4) Date: Oct. 23, 2009

(87) PCT Pub. No.: WO2008/134430
PCT Pub. Date: Nov. 6, 2008

(65) Prior Publication Data
US 2010/0087393 A1     Apr. 8, 2010

Related U.S. Application Data

(60) Provisional application No. 60/913,643, filed on Apr. 24, 2007.

(51) Int. Cl.
*A61K 31/70* (2006.01)
*A61K 45/06* (2006.01)
*A61K 31/737* (2006.01)

(52) U.S. Cl.
CPC .............. *A61K 31/737* (2013.01); *A61K 45/06* (2013.01); *Y10S 514/825* (2013.01); *Y10S 514/866* (2013.01)

(58) Field of Classification Search
CPC .... A61K 31/70; A61K 45/06; A61K 2300/00

USPC .............. 514/15.1, 59, 54, 825, 866; 606/132
See application file for complete search history.

(56) References Cited

U.S. PATENT DOCUMENTS

| | | | | |
|---|---|---|---|---|
| 6,686,341 | B1 * | 2/2004 | Bijlsma et al. | 514/54 |
| 7,071,213 | B2 * | 7/2006 | Friary et al. | 514/323 |
| 2005/0175665 | A1 * | 8/2005 | Hunter et al. | 424/423 |

FOREIGN PATENT DOCUMENTS

WO     WO 02083130 A1 * 10/2002

OTHER PUBLICATIONS

Banz, y, et al. "Locally targeted cytoprotection with dextran sulfate attenuates experimental porcine myocardial ischaemia/reperfusion injury". Eur. Heart. J. Nov. 2005. vol. 26, No. 21, pp. 2334-2343; abstract; p. 2335, para 1, 5; p. 2337, para 8; p. 2341, para 1.
Ercan, E. et al., Decreased soluble cell adhesion molecules after tirofiban infusion in patients with unstable angina pectoris. Thromb. J. Apr. 1, 2004, vol. 2, No. 2, pp. 4-9; abstract.
Dohi, K. et al. "Mesangial proliferative glomerulonephritis, Natural history and effects of dextran sulfate". Jpn. J. Med. Feb. 1987, vol. 26, No. 1, pp. 50-57.
Johansson, H. et al. "Low molecular weight dextran sulfate: a strong candidate drug to block IBMIR in clinical islet transplantation", Am. J. Transplant. Feb. 2006, vol. 6, No. 2, pp. 305-312.
Kelegeris, A. et al. "Effects of C-reactive protein and pentosan polysulphate on human complement activation", Immunology. Jul. 2005, vol. 106, No. 3, pp. 381-388.

* cited by examiner

*Primary Examiner* — Brandon Fetterolf
*Assistant Examiner* — Everett White
(74) *Attorney, Agent, or Firm* — Tarolli, Sundheim, Covell & Tummino LLP

(57) ABSTRACT

A method of inhibiting the adverse effects of complement pathway, activation products in a subject comprising administering to the subject an amount of Dextran Sulfate effective to inhibit formation of alternative complement pathway activation product.

4 Claims, 15 Drawing Sheets

METHODS AND COMPOSITIONS OF INHIBITING COMPLEMENT AND CELLULAR ACTIVATION WITH DEXTRAN SULFATE

RELATED APPLICATION

This application claims priority from U.S. Provisional Application No. 60/913,643, filed Apr. 24, 2007, the subject matter, which is incorporated, herein by reference.

TECHNICAL FIELD

The present invention relates to a new use of Dextran Sulfate for the treatment of acute and chronic clinical conditions, and particularly relates to the use of Dextran Sulfate alone or in combination with an antiplatelet agent for inhibiting complement, coagulation, and platelet activation.

BACKGROUND OF THE INVENTION

Complement is activated by three pathways, the classical pathway, the alternative pathway, and the recently discovered lectin pathway, all of which lead to the formation of the cytolytic membrane attack complex, C5b-9. Following complement activation, the biologically active peptides C5a and C3a elicit a number of proinflammatory effects, such as chemotaxis of leukocytes, degranulation of phagocytic cells, mast cells, and basophils, smooth muscle contraction, and increase of vascular permeability. Upon activation by these complement products; the inflammatory response is further amplified by subsequent generation of toxic oxygen radicals, induction of synthesis, and release of arachidonic acid metabolites and cytokines. Consequently, an (over)activated complement system presents a considerable risk of harming the host by directly and indirectly mediating inflammatory tissue destruction. The key proteins involved in the activation of the alternative pathway are factors P, B and factor D. These proteins work together to amplify the activation of C3, which then leads to the initiation of a number of inflammatory events.

The trigger of the alternative complement pathway is artificial surfaces including bacteria, parasites, viruses or fungi. Alternative pathway activation is triggered when factor B binds to C3b or C3H2O. This complex is then cleaved by factor D to produce C3 convertase (C3bBb). The alternative pathway C3 convertase is stabilized by the binding of properdin, extending its half-life six-to ten-fold. An amplification loop is established as the C3 convertase generates increasing amounts of C3b. The classical pathway can also generate C3b, which can engage the alternative pathway by binding factor B. Addition of C3b to the C3 convertase (PC3bBb) leads to the formation of the alternative pathway C5 convertase, PC3bBbC3b. All three pathways, the classical, lectin, and alternative converge at C3, which is cleaved by C3 convertase to form C3a with multiple pro-inflammatory effects. C5a and C5b are formed by the cleavage of C5. The C5b associates with the cell membrane and ultimately becomes the part of membrane attack complex C5b-9 (MAC), which is now thought to play an important role in inflammation as well as a lytic pore-forming complex.

Split products of both C3 and C5 designated as C3a and C5a are potent anaphylatoxins and are responsible for activating neutrophils, monocytes, and platelets. These activated cells indiscriminately release destructive enzymes that have the capacity to cause significant organ damage. Anaphylatoxins can significantly amplify inflammatory responses by inducing the release of numerous additional inflammatory mediators, including cytokines, hydrolytic enzymes, arachidonic acid metabolites, and reactive oxygen species from neutrophils and monocytes. C3a is a potent anaphylatoxin which can initiate detrimental events, including the release of pro-inflammatory cytokines (Takabayashi, T., et al., A new biologic role for C3a and C3a desArg: regulation of TNF-alpha and IL-1 beta synthesis. J Immunol, 1996. 156(9): p. 3455-60) and prostaglandins (Howard, R. J., et al., Effects of cardiopulmonary bypass on pulmonary leukostasis and complement activation. Arch Surg, 1988. 123(12): p. 1496-501) from monocytes, activation of monocytes (Haeffner-Cavaillon, N., et al., C3a(C3adesArg) induces production and release of interleukin 1 by cultured human monocytes. J Immunol, 1987. 139(3): p. 794-9; Rinder, C. S., et al., Role of C3 cleavage in monocyte activation during extracorporeal circulation. Circulation, 1999. 100(5): p. 553-8) histamine release from mast cells, and de-granulation of eosinophils (Krug, N., et al., Complement factors C3a and C5a are increased in bronchoalveolar lavage fluid after segmental allergen provocation in subjects with asthma. Am J Respir Crit Care Med, 2001. 164(10 Pt 1): p. 1841-3). C3a plays a significant role in cognition and memory (Hugli, T. E., The structural basis for anaphylatoxin and chemotactic functions of C3a, C4a, and C5a. Crit Rev Immunol, 1981. 1(4): p. 321-66; van Beek, J., K. Elward, and P. Gasque, Activation of complement in the central nervous system: roles in neurodegeneration and neuroprotection. Ann N Y Acad Sci, 2003. 992: p. 56-71). C3a receptors are mainly found on neutrophils and monocytes (Gerardy-Schahn, R., et al., Characterization of C3a receptor-proteins on guinea pig platelets and human polymorphonuclear leukocytes. European Journal of Immunology, 1989. 19(6): p. 1095; Cecic, I., J. Sun, and M. Korbelik, Role of complement anaphylatoxin C3a in photodynamic therapy-elicited engagement of host neutrophils and other immune cells. Photochem Photobiol, 2006. 82(2): p. 558-62). Increased levels of C3a in the circulation have been found in diseases such as the adult respiratory distress syndrome (Solomkin, J. S., et al., Complement activation and clearance in acute illness and injury: evidence for C5a as a cell-directed mediator of the adult respiratory distress syndrome in man. Surgery, 1985. 97(6): p. 668-78; Abe, M., [Complement activation and inflammation]. Rinsho Byori, 2006. 54(7): p. 744-56), rheumatoid arthritis (Rinsho Byori, 2006. 54(7): p. 744-56), psoriasis (Rinsho Byori, 2006. 54(7): p. 744-56; Kapp, A., H. Wokalek, and E. Schopf, Involvement of complement in psoriasis and atopic dermatitis—measurement of C3a and C5a, C3, C4 and C1 inactivator. Arch Dermatol Res, 1985. 277(5): p. 359-61) and atopic dermatitis (Arch Dermatol Res, 1985. 277(5): p. 359-61). C3a is also found intralesionally in inflammatory diseases, e.g. psoriasis (Takematsu, H., K. Ohkohchi, and H. Tagami, Demonstration of anaphylatoxins C3a, C4a and C5a in the scales of psoriasis and inflammatory pustular dermatoses. Br J Dermatol, 1986. 114(1): p. 1-6), eczema (Br J Dermatol, 1986. 114(1): p. 1-6), and asthma (Am J Respir Crit Care Med, 2001. 164(10 Pt 1): p. 1841-3; Rinsho Byori, 2006. 54(7): p. 744-56; Marc, M. M., et al., Complement factors c3a, c4a, and c5a in chronic obstructive pulmonary disease and asthma. American Journal of Respiratory Cell and Molecular Biology, 2004. 31(2): p. 216; Zaidi, A. K., et al., Response to C3a, mast cells, and asthma. Faseb J, 2006. 20(2): p. 199; Humbles, A. A., et al., A role for the C3a anaphylatoxin receptor in the effector phase of asthma. Nature, 2000. 406(6799): p. 998-1001).

Inappropriate activation of the complement system contributes to pathogenesis of numerous acute and chronic disease states, including Myocardial Infarction, Reperfusion Injury, Stroke, ARDS, Hemodialysis, Plasmapheresis, leukopheresis, Cardiopulmonary bypass, Rheumatoid arthritis, systemic lupus erythematosus (SLE), osteoarthritis, lupus, membranous nephritis, Myasthenia Gravis, pancreatitis, Septic Shock, Multiple Sclerosis, Alzheimer's Disease, Traumatic Brain Injury, Spinal Cord Injury, Neuropathic Pain, Neurological Injury, spontaneous abortion, miscarriages, Transplant Rejection, Asthma, Cancer, Thermal Burn. Despite the role of complement in several disease indications, no drug currently exists to downregulate this complement activation.

The following are disorders associated with complement activation: systemic inflammatory reaction syndrome, multiple organ dysfunction syndrome, ischemia-reperfusion syndrome, angioedema, capillary leak syndrome, hyperacute and acute graft rejection, vasculitis, nephritis, autoimmune disorders (e.g., SLE, rheumatoid arthritis, and myasthenia gravis), biomaterial incompatibility (e.g., following dialysis or cardiopulmonary bypass), and severe trauma, burn, and sepsis. Only recently has complement also been implicated in neurodegenerative disorders, such as Alzheimer's disease (Ann N Y Acad Sci, 2003. 992: p. 56-71; Zanjani, H., et al., Complement activation in very early Alzheimer disease. Alzheimer Disease and Associated Disorders, 2005. 19(2): p. 55), multiple sclerosis (Sanders, M. E., et al., Activated terminal complement in cerebrospinal fluid in Guillain-Barre syndrome and multiple sclerosis. J Immunol, 1986. 136(12): p. 4456-9), Guillain-Barré syndrome (J Immunol, 1986. 136 (12): p. 4456-9), traumatic brain injury and spinal cord injury (Bellander, B. M., et al., Complement activation in the human brain after traumatic head injury. J Neurotrauma, 2001. 18(12): p. 1295-311; Leinhase, I., et al., Inhibition of the alternative complement activation pathway in traumatic brain injury by a monoclonal anti-factor B antibody: a randomized placebo-controlled study in mice. J Neuroinflammation, 2007. 4: p. 13; Stahel, P. F., et al., Intrathecal levels of complement-derived soluble membrane attack complex (sC5b-9) correlate with blood-brain barrier dysfunction in patients with traumatic brain injury. J Neurotrauma, 2001. 18(8): p. 773-81; Schmidt, O. I., et al., [The relevance of the inflammatory response in the injured brain]. Orthopade, 2007. 36(3): p. 248, 250-8; Morganti-Kossmann, M. C., et al., Role of cerebral inflammation after traumatic brain injury: a revisited concept. Shock, 2001. 16(3): p. 165-77; Stahel, P. F., M. C. Morganti-Kossmann, and T. Kossmann, The role of the complement system in traumatic brain injury. Brain Res Brain Res Rev, 1998. 27(3): p. 243-56). Furthermore, activation of complement is a critical event in the pathogenesis of sepsis and septic shock (Bengston, A., Heideman, M, Anaphylatoxin formation in sepsis. Arch Surg, 1988. 123: p. 645-649; Laudes, I. J., et al., Anti-c5a ameliorates coagulation/fibrinolytic protein changes in a rat model of sepsis. American Journal Of Pathology, 2002. 160(5): p. 1867; Hack, C. E., et al., A model for the interplay of inflammatory mediators in sepsis—a study in 48 patients. Intensive Care Med, 1990. 16 Suppl 3: p. S187-91). Complement activation after polytrauma substantially contributes to the development of systemic inflammatory reaction syndrome and multiple organ failure (Kirschfink, M., Controlling the complement system in inflammation. Immunopharmacology, 1997. 38(1-2): p. 51-62; Sistino, J. J. and J. R. Acsell, Systemic inflammatory response syndrome (SIRS) following emergency cardiopulmonary bypass: a case report and literature review. J Extra Corpor Technol, 1999. 31(1): p. 37-43). In recent years, complement has been recognized as a major effector mechanism of reperfusion injury. The inflammatory response induced by artificial surfaces in hemodialysis and extracorporeal circuits may lead to organ dysfunction. Here, complement activation has been shown to be associated with transient neutropenia, pulmonary vascular leukostasis, and occasionally, anaphylactic shock of variable severity in patients undergoing hemodialysis or cardiopulmonary bypass (Immunopharmacology, 1997. 38(1-2): p. 51-62; Chenoweth, D. E., Anaphylatoxin formation in extracorporeal circuits. Complement, 1986. 3(3): p. 152-65; Hammerschmidt, D. E., et al., Complement activation and neutropenia occurring during cardiopulmonary bypass. J Thorac Cardiovasc Surg, 1981. 81(3): p. 370-7; Lin, Y. F., et al., Cytokine production during hemodialysis: effects of dialytic membrane and complement activation. Am J Nephrol, 1996. 16(4): p. 293-9; Chenoweth, D. E., et al., Complement activation during cardiopulmonary bypass: evidence for generation of C3a and C5a anaphylatoxins. N Engl J Med, 1981. 304(9): p. 497-503; Tamiya, T., et al., Complement activation in cardiopulmonary bypass, with special reference to anaphylatoxin production in membrane and bubble oxygenators. Ann Thorac Surg, 1988. 46(1): p. 47-57; Chello, M., et al., Complement and neutrophil activation during cardiopulmonary bypass: a randomized comparison of hypothermic and normothermic circulation. Eur J Cardiothorac Surg, 1997. 11(1): p. 162-8; Levy, J. H. and K. A. Tanaka, Inflammatory response to cardiopulmonary bypass. Ann Thorac Surg, 2003. 75(2): p. S715-20).

In recent years, great progress has been made in complement analysis to better define disease severity, evolution, and response to therapy. Modern diagnostic technologies, which focus on the quantification of complement-derived split products or protein-protein complexes, now provide comprehensive insight into the activation state of the system. In certain vasculitides and kidney diseases, a substantial activation and consumption of C3 due to defective alternative pathway regulation can be observed. Patients suffering from MPGN, show low levels of CH50, AH50, and C3. This results from a continuous C3 activation due to an autoantibody, termed C3 nephritic factor (C3NeF), which stabilizes the labile C3bBb complex (Jelezarova, E., et al., A C3 convertase assay for nephritic factor functional activity. J Immunol Methods, 2001. 251(1-2): p. 45-52).

Role of Coagulation and Fibrinolysis in CPB

Coagulation/and platelet activation cascades are initiated during cardiopulmonary bypass (CPB) based on the reported production of thrombin and platelet activation markers upon blood exposure to artificial surfaces (Edmunds, L. H., Jr. and R. W. Colman, Thrombin during cardiopulmonary bypass. Ann Thorac Surg, 2006. 82(6): p. 2315-22). Thrombotic and bleeding complications seem to be caused by generation of thrombin during cardiopulmonary bypass. Thrombin generation and the fibrinolytic response primarily involve the extrinsic and intrinsic coagulation pathways, the contact and fibrinolytic plasma protein systems, and platelets, monocytes, and endothelial cells. Thrombin is generated because of extracorporeal circulation and varies with the amount and type of anticoagulant used.

Due to increasing evidence, there are indications that the wound is the major generation source of thrombin during CPB and clinical cardiac surgery. Endothelial cells are activated by circulating thrombin, to produce tissue plasminogen activator (t-PA), which binds fibrin. Endothelial cells are the principal source of t-PA, which when combined with fibrin and plasminogen, cleaves plasminogen to plasmin; plasmin cleaves fibrin. This reaction produces the useful marker of fibrinolysis, protein fragment, and D-dimer. D-dimer increases during extracorporeal perfusion, indicating ongoing thrombin production, fibrin formation, and fibrinolysis.

Heparin, the anticoagulant drug most often employed first in the prevention and treatment of thromboembolic diseases, causes heparin-induced thrombocytopenia (HIT) a special class of platelet thrombosis that occurs as an immune response to the drug. The morbidity and mortality of HIT patients remains high, while standard treatment of HIT involves discontinuing heparin and the use of an alternative anticoagulant, such as a thrombin inhibitor, followed by close platelet count monitoring for the recovery. Recently, despite the use of alternatives, a standard dose of GPIIb/IIIa antagonist, combined with a lowered dose of thrombin inhibitor to minimize hemorrhagic events, was used to treat HIT thrombosis (Walenga, J. M., et al., Clinical experience with combined treatment of thrombin inhibitors and GPIIb/IIIa inhibitors in patients with HIT. Semin Thromb Hemost, 1999. 25 Suppl 1: p. 77-81). A fibrinolytic-resistant re-thrombosis that is platelet-rich often occurs, despite tendencies of initial thrombosis of the coronary arteries being susceptible to treatment with fibrin-dissolving agents, such as tissue plasminogen activator or streptokinase. Combination of thrombin inhibitors with the use of fast-acting antiplatelet drugs such as GPIIb/IIIa antagonists is often necessary to control the local generation of active thrombin. However, combination of improved anticoagulants with the GPIIb/IIIa antagonists are needed in the treatment of HIT and other thrombo-embolic disorders. Surface-bound thrombin at residual levels amplifies the generation of systemic thrombin by catalyzing pro-thrombin consumption via the thrombin feedback loop at the site of vascular injury (Fenton, J. W., 2nd, et al., Understanding thrombin and hemostasis. Hematol Oncol Clin North Am, 1993. 7(6): p. 1107-19; Ofosu, F. A., Anticoagulant actions of tissue factor pathway inhibitor on tissue-factor-dependent plasma coagulation. Semin Thromb Hemost, 1995. 21(2): p. 240-4; Ofosu, F. A., et al., Inhibition of the amplification reactions of blood coagulation by site-specific inhibitors of alpha-thrombin. Biochem J, 1992. 283(Pt 3): p. 893-7). Moreover, when thrombin is generated in response to an injury or disease, it can be found in the systemic circulation or fluid phase, as well as associated with the fibrin clot, cell surfaces, such as platelets, the vessel wall, and the biomaterial surfaces of biometric circuits and devices.

Expression of GPIIb/IIIa receptors on the surface of activated platelets greatly enhances their, aggregation and adherence to the fibrin clot and injured vessel wall. Thus, thrombin-activated platelets promote thrombus growth indicating a need for improved thrombin inhibitors with antiplatelet therapies (Eisenberg, P. R. and G. Ghigliotti, Platelet-dependent and procoagulant mechanisms in arterial thrombosis. Int J Cardiol, 1999. 68 Suppl 1: p. S3-10).

SUMMARY OF THE INVENTION

The present invention relates to compositions and methods that can inhibit complement activation, thrombin generation, and platelet aggregation with minimized or reduced hemorrhagic properties and high selectivity for surface-bound thrombin inhibition.

One aspect of the invention relates to the use of Dextran Sulfate for inhibiting complement activation in a subject by inhibiting properdin from binding C3b, C3bB, or C3bBb, C3bBbB. The Dextran Sulfate molecule can be of varying molecular weights and prevent factor P binding to C3b, inhibit the assembly of C3 convertase (PC3bBb), or inhibit assembly of C5 convertase (PC3bBbBb). In an aspect of the invention the Dextran Sulfate can have a molecular weight greater than about 400 (e.g., about 1000) but less that 500 kDa (e.g., about 1000 Daltons to about 500,000 Daltons).

The Dextran Sulfate can be administered to a subject alone or in combination with a compound that prevents platelet activation and/or platelet aggregation (i.e., an antiplatelet agent) to treat a clinical condition associated with complement activation. This can be done in a combined dose or as separate related doses and with the intention to prevent and/or treat a variety of complement-mediated and thromboembolic disorders. It is proposed that the administration of a combined therapeutically effective amount of Dextrane Sulfate with thrombin inhibitory properties and molecules that prevent platelet activation and/or platelet aggregation can provide a superior therapeutic effect in numerous areas. These surprising therapeutic benefits can be achieved while creating reduced risk of hemorrhagic side effects, such as prolonged bleeding.

The present invention also relates to a method of inhibiting the adverse effects of complement pathway activation products in a subject. The method includes administering to the subject an amount of Dextran Sulfate effective to inhibit formation of alternative complement pathway activation product.

In an aspect of the invention, the Dextran Sulfate can have a molecular weight of about 1000 Daltons to about 500,000 Daltons. The Dextran Sulfate can be administered to the subject at an amount effective to inhibit at least one of: formation of MAC, formation of alternative pathway derived C3a, C3b, and C5a, activation of immune cells, neutrophils, and monocytes, or formation of thrombin.

In a further aspect, an antiplatelet agent can be administered to the subject in combination with the Dextran Sulfate. The antiplatelet agent can be administered at an amount effect to inhibit platelet activation. The antiplatelet agent can include at least one of a COX inhibitor, ticlopidine, clopidogrel, or GPIIb/IIIa inhibitor. The antiplatelet agent can also include a GPIIb/IIIa receptor antagonist.

The present invention also relates to a method of treating a subject suffering from complement mediated clinical condition. The method includes administering to the subject an amount of Dextran Sulfate effective to inhibit alternative pathway-dependent complement activation.

In an aspect of the invention, the Dextran Sulfate can have a molecular weight of about 1000 Daltons to about 500,000 Daltons. The Dextran Sulfate can be administered to the subject at an amount effective to inhibit at least one of: formation of MAC, formation of alternative pathway derived C3a, C3b, and C5a, activation of immune cells, neutrophils, and monocytes, or formation of thrombin.

In a further aspect, an antiplatelet agent can be administered to the subject in combination with the Dextran Sulfate. The antiplatelet agent can be administered at an amount effective to inhibit platelet activation. The antiplatelet agent can include at least one of a COX inhibitor, ticlopidine, clopidogrel, or GPIIb/IIIa inhibitor. The antiplatelet agent can also include a GPIIb/IIIa receptor antagonist.

In another aspect, the clinical condition can be selected from the group consisting of a Myocardial Infarction, Reperfusion Injury, Stroke, ARDS, Hemodialysis, Plasmapheresis, leukopheresis, Cardiopulmonary bypass, Rheumatoid arthritis, systemic lupus erythematosus (SLE), osteoarthritis, lupus, membranous nephritis, Myasthenia Gravis, pancreatitis, Septic Shock, Multiple Sclerosis, Alzheimer's Disease, Traumatic Brain Injury, Spinal Cord Injury, Neuropathic Pain, Neurological Injury, spontaneous abortion, miscarriages, Transplant Rejection, Asthma, Cancer, Thermal Burn.

The clinical condition can also be associated with an ischemia-reperfusion injury. The ischemia-reperfusion injury can be associated with an aortic aneurysm repair, cardiopulmonary bypass, vascular reanastomosis in connection with organ transplants and/or extremity/digit replantation, stroke, myocardial infarction, and hemodynamic resuscitation following shock and/or surgical procedures.

In another aspect, the clinical condition can comprise an inflammatory gastrointestinal disorder. The inflammatory gastrointestinal disorder can be selected from the group consisting of pancreatitis, Crohn's disease, ulcerative colitis, irritable bowel syndrome and diverticulitis.

In a further aspect, the clinical condition can comprise a complement mediated pulmonary condition. The pulmonary condition can be selected from the group consisting of acute respiratory distress syndrome, transfusion-related acute lung injury, ischemia/reperfusion acute lung injury, chronic obstructive pulmonary disease, asthma, Wegener's granulomatosis, antiglomerular basement membrane disease (Goodpasture's disease), meconium aspiration syndrome, bronchiolitis obliterans syndrome, idiopathic pulmonary fibrosis, acute lung injury secondary to burn, non-cardiogenic pulmonary edema, transfusion-related respiratory depression and emphysema.

In yet another aspect, the clinical condition can include an extracorporeal reperfusion procedure. The extracorporeal reperfusion procedure can be selected from the group consisting of hemodialysis, plasmapheresis, leukopheresis, extracorporeal membrane oxygenator (ECMO), heparin-induced extracorporeal membrane oxygenation LDL precipitation (HELP) and cardiopulmonary bypass (CPB).

In another aspect, the clinical condition can include a musculoskeletal condition. The musculoskeletal condition can be selected from the group consisting of osteoarthritis, rheumatoid arthritis, gout, neuropathic arthropathy, psoriatic arthritis, juvenile rheumatoid arthritis, spondyloarthropathy, crystalline arthropathy and systemic lupus erythematosus (SLE).

In a further aspect, the clinical condition can include an AP-dependent complement mediated renal condition. The renal condition can be selected from the group consisting of mesangioproliferative glomerulonephritis, membranous glomerulonephritis, membranoproliferative glomerulonephritis (mesangiocapillary glomerulonephritis), acute postinfectious glomerulonephritis (poststreptococcal glomerulonephritis), cryoglobulinemic glomerulonephritis, lupus nephritis, Henoch-Schonlein purpura nephritis and IgA nephropathy.

In a still further aspect, the clinical condition can include an AP-dependent complement mediated skin condition. The skin condition can be selected from the group consisting of psoriasis, autoimmune bullous dermatoses, eosinophilic spongiosis, bullous pemphigoid, epidermolysis bullosa acquisita, herpes gestationis, thermal burn injury and chemical burn injury.

In another aspect, the clinical condition can include an organ or tissue transplantation. The transplant procedure can be selected from the group consisting of organ allotransplantation, organ xenotransplantation organ and tissue graft.

In yet another aspect the clinical condition can include an AP-dependent complement mediated condition associated with a nervous system disorder or injury. The nervous system disorder or injury can be selected from the group consisting of multiple sclerosis, myasthenia gravis, Huntington's disease, amyotrophic lateral sclerosis, Guillain Barre syndrome, reperfusion following stroke, degenerative discs, cerebral trauma, Parkinson's disease, Alzheimer's disease, MillerFisher syndrome, cerebral trauma and/or hemorrhage, demyelination and meningitis.

In a further aspect, the clinical condition can include an AP-dependent complement mediated condition associated with a blood disorder. The blood disorder can be selected from the group consisting of sepsis, severe sepsis, septic shock, acute respiratory distress syndrome resulting from sepsis, systemic inflammatory response syndrome, hemorrhagic shock, hemolytic anemia, autoimmune thrombotic thrombocytopenic purpura and hemolytic uremic syndrome.

In yet another aspect, the clinical condition can include an AP-dependent complement mediated condition associated with a urogenital condition. The urogenital condition can be selected from the group consisting of painful bladder disease, sensory bladder disease, chronic bacterial cystitis, interstitial cystitis, infertility, placental dysfunction and miscarriage and pre-eclampsia.

In yet another aspect, the clinical condition can include an AP-dependent complement mediated condition associated with non-obese diabetes (Type-1 diabetes or Insulin-dependent diabetes mellitus) and/or complications associated with Type-1 or Type-2 (adult onset) diabetes. The complication associated with Type 1 or Type 2 diabetes can be selected from the group consisting of angiopathy, neuropathy and retinopathy.

In another aspect, the subject can have undergone, is undergoing, or will undergo chemotherapeutic treatment and/or radiation therapy.

In a further aspect, the clinical condition can include an endocrine disorder. The endocrine disorder can be selected from the group consisting of Hashimoto's thyroiditis, stress, anxiety and hormonal disorders involving regulated release of prolactin, growth or other insulin-like growth factor and adrenocorticotropin from the pituitary.

In another aspect, the clinical condition can include a complement mediated ophthalmologic condition. The ophthalmologic condition can be age-related macular degeneration.

In still another aspect, the clinical condition can include an autoimmune disease selected from the group consisting of rheumatoid arthritis, osteoarthritis, multiple sclerosis, myasthenia gravis, pancreatitis, rheumatoid arthritis, Alzheimer's disease, asthma, lupus erythromatosus, spontaneous abortion, miscarriages and membranous nephritis.

The present invention also relates to a method of treating a subject suffering from complement mediated clinical condition. The method includes administering to the subject an amount of Dextran Sulfate effective to inhibit alternative pathway-dependent complement activation and an amount of a antiplatelet agent effective to inhibit platelet activation and/or platelet aggregation.

In an aspect of the invention, the Dextran Sulfate can have a molecular weight of about 1000 Daltons to about 500,000 Daltons. The Dextran Sulfate can be administered to the subject at an amount effective to inhibit at least one of: formation of MAC, formation of alternative pathway derived C3a, C3b, and C5a, activation of immune cells, neutrophils, and monocytes, or formation of thrombin.

The antiplatelet agent can be administered at an amount effective to inhibit platelet activation. The antiplatelet agent includes at least one of a COX inhibitor, ticlopidine, clopidogrel, or GPIIb/IIIa inhibitor. The antiplatelet agent can also include a GPIIb/IIIa receptor antagonist.

The present invention further relates to a method of treating a subject suffering from an ischemia-reperfusion injury. The method includes administering to the subject an amount of Dextran Sulfate effective to inhibit alternative pathway-dependent complement activation and an amount of an antiplatelet agent effective to inhibit platelet activation and/or platelet aggregation.

In an aspect of the invention, the Dextran Sulfate can have a molecular weight of about 1000 Daltons to about 500,000 Daltons. The Dextran Sulfate can be administered to the subject at an amount effective to inhibit at least one of: formation of MAC, formation of alternative pathway derived C3a, C3b, and C5a, activation of immune cells, neutrophils, and monocytes, or formation of thrombin.

The antiplatelet agent can be administered at an amount effective to inhibit platelet activation. The antiplatelet agent includes at least one of a COX inhibitor, ticlopidine, clopidrogrel, or GPIIb/IIIa inhibitor. The antiplatelet agent can also include a GPIIb/IIIa receptor antagonist.

The ischemia-reperfusion injury can be associated with aortic aneurysm repair, cardiopulmonary bypass, vascular reanastomosis in connection with organ transplants and/or extremity/digit replantation, stroke, myocardial infarction, and hemodynamic resuscitation following shock and/or surgical procedures.

The present invention future relates to a pharmaceutical composition for treating a complement mediated clinical condition. The pharmaceutical composition includes an amount of Dextran Sulfate effective to inhibit alternative pathway-dependent complement activation and an amount of an antiplatelet agent effective to inhibit platelet activation and/or platelet aggregation.

In an aspect of the invention, the Dextran Sulfate can have a molecular weight of about 1000 Daltons to about 500,000 Daltons. The antiplatelet agent includes at least one of COX inhibitor, ticlopidine, clopidrogrel, or GPIIb/IIIa inhibitor. The antiplatelet agent can also include a GPIIb/IIIa receptor antagonist.

Figure 7:
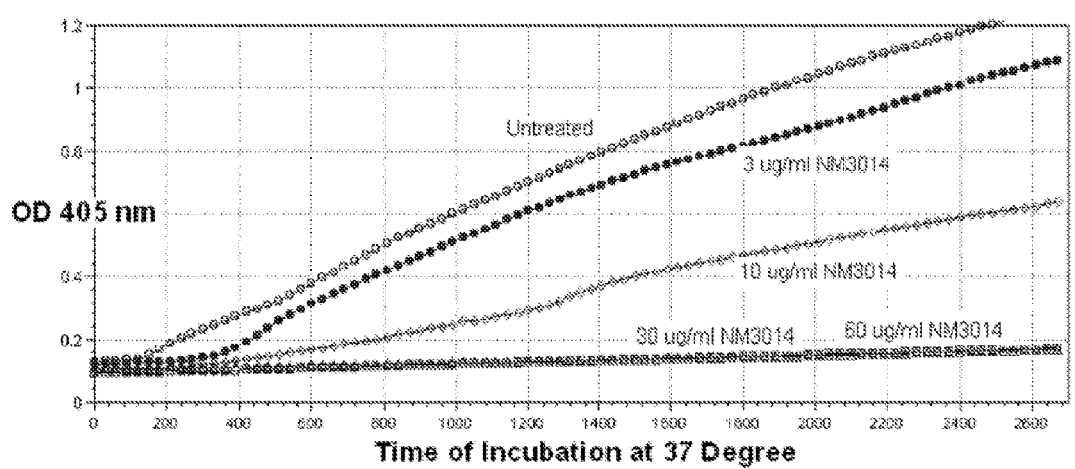

FIG. 7 illustrates NM33014 Inhibits Thrombin Generation in Citrated Human plasma: Citrated Human Plasma was mixed with various concentrations of Dextran Sulfate in the presence of constant concentration of S2238 (Diapharma). This mixture was treated with an optimal dose of innovin (aPTT reagent from Dade Behring, Innovin initiates the tissue factor pathway of coagulation. As a result, thrombin is produced which reacts with S-2238 to generate yellow color. S2238 reacts with thrombin as it is being produced. The first line from the top is without Dextran Sulfate addition (untreated). The second line contains 3 µg/ml of Dextran Sulfate, the third line contains 10 µg/ml of Dextran Sulfate, the fourth line consists of two different lines representing 30 µg/ml and 60 µg/ml of Dextran Sulfate. NM3014 at 60 and 30 µg/ml inhibit coagulation. A 10 µg/ml appears to have a partial effect on coagulation. Data was recorded using Soft Max-Pro on Spectramax 190 kinetic spectramax. Data presented is from a representative experiment that was repeated three times.

Figure 8:
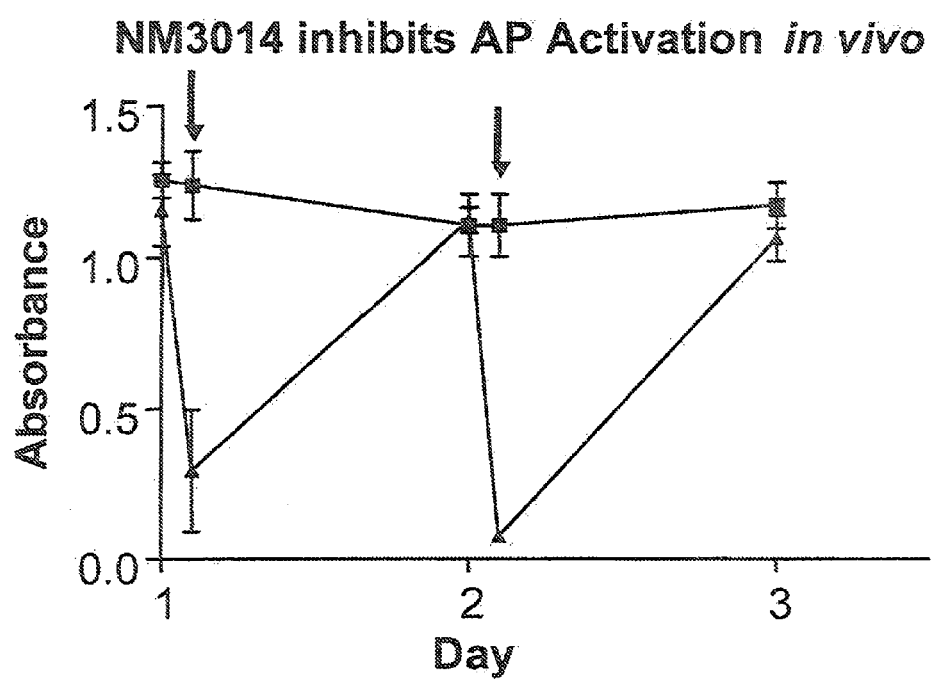

FIG. 8 illustrates NM3014 Inhibits Complement Activity in Antigen-Induced Arthritic Rabbit treated with NM3014 i.v: Dextran Sulfate treated animals had significantly lower complement activation compared to vehicle-treated rabbits with AIA. The data compares NM3014 treated animals versus saline treated controls. METHODS: After the intra-articular ovalbumin injection to induce arthritis, disease pathology developed for seven days prior to the collection of a blood sample to determine complement activation levels and the administration of Dextran Sulfate treatment. Blood samples were drawn prior to all treatments with Dextran Sulfate to establish baseline values and pre-treatment complement activation levels. Dextran Sulfate (60 mg/Kg) was then injected via the marginal vein every day over a 3 day period. Ten minutes after treatment with Dextran Sulfate a second 1-ml blood sample from the ear to assess complement activation shortly after the treatment. Complement activation was assessed using the C3c assay described in methods. There appears to be a complete inhibition of complement activity in vivo.

Figure 9:
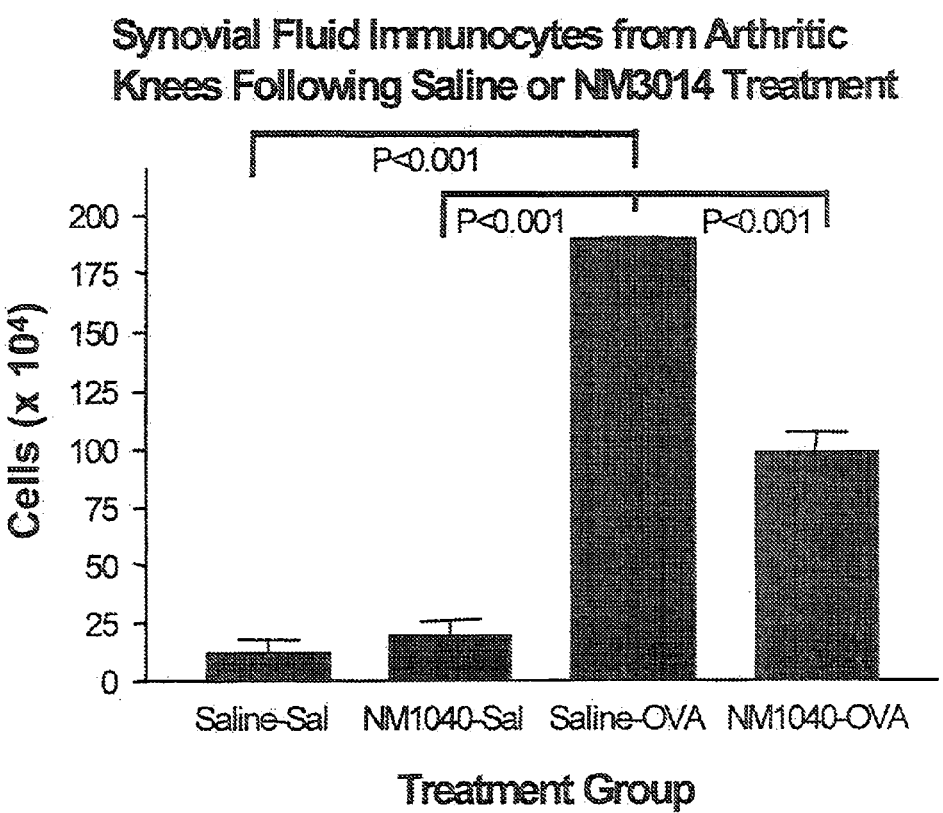

FIG. 9 illustrates NM3014 Cellular Infiltration into Arthritic Joints in Rabbits: Immunocyte homing into the Arthritic joints was reduced in Dextran Sulfate-treated compared to vehicle-treated AIA rabbits. Methods. The numbers of immune cells infiltrating the synovial fluid of the right and left joints was determined by cell counting using a hemocytometer.

Figure 10:
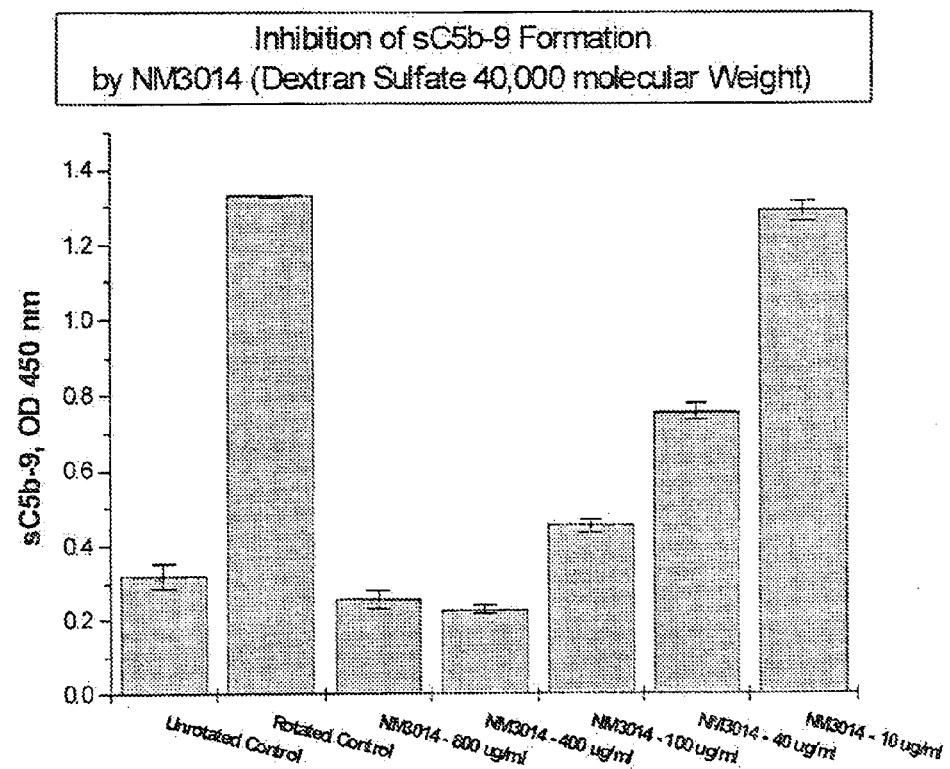

FIG. 10 illustrates NM3014 Inhibits sC5b-9 in Normal Heparinized Whole Human Blood in Extra Corporeal Circulation (Tubing Loop) Model of Cardiopulmonary Bypass. An aliquot of the plasma following the 2 hour tubing loop rotation in bypass was evaluated for sC5b-9 using ELISA kit from Quidel Corporation. Blood samples treated with 800, 400, and 100 µg/ml concentration of NM3014 (Dextrans Sulfate 40K) demonstrated complete inhibition of sC5b-9 formation. A concentration of NM3014 at 40 µg/ml demonstrated no inhibition of sC5b-9 formation. An aliquot of blood samples were also tested for neutrophil, monocyte and platelet activation. Both neutrophil and monocyte activation was inhibited but platelets demonstrated an increased CD62P staining. A dose of 100 µg/ml was chosen to evaluate the effect of aspirin and a neutralizing GPIIb/IIIa antibody on inhibition of platelet activation.

Figure 10A:
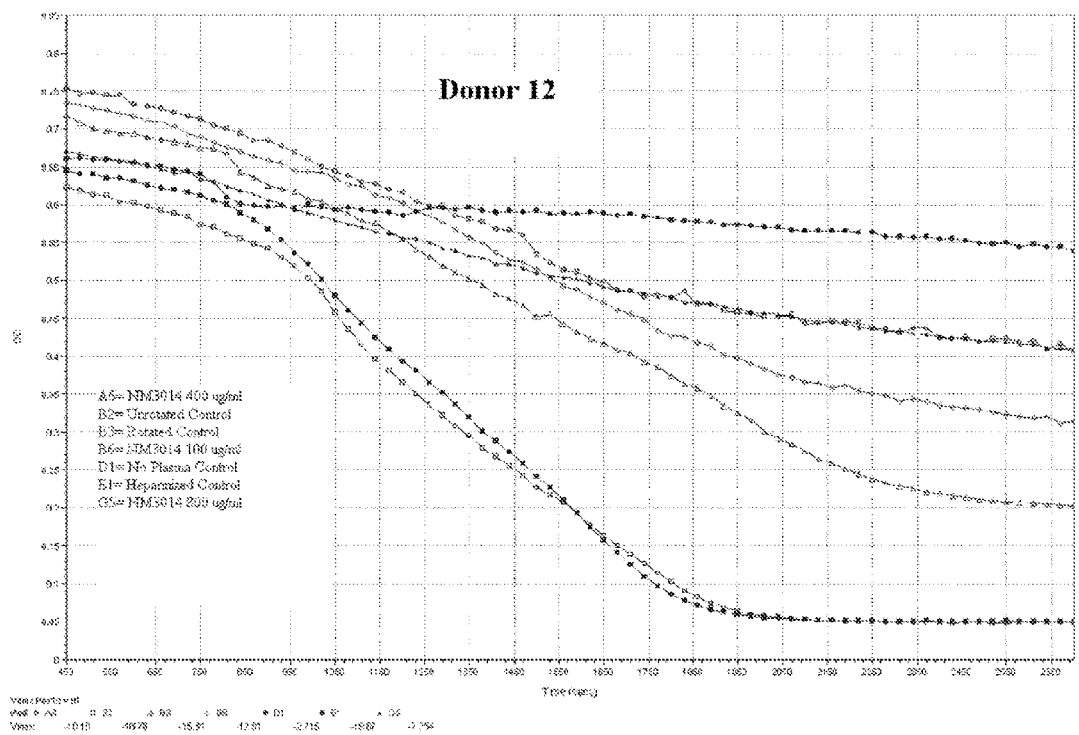

FIG. 10a illustrates NM3014 Inhibits Complement Activity in Whole Blood Following Tubing Loop Model: Samples of plasma after the tubing loop model were incubated with rabbit erythrocytes and incubated for 2700 seconds. Light-scattering was measured as a function of time. The first line starting from the bottom is un-rotated control (samples without tubing loop processing), the second line is from heparinized control from the same donor (diluted to the same level of plasma with plasmalyte), the third line represents samples following tubing loop rotation (rotated control), the fourth line contains 100 µg/ml NM3014, the fifth line contains 400 µg/ml of NM3014, and the sixth line contains 800 µg/ml of NM3014. X-axis is time of hemolysis in seconds and Y-axis is scattering at 700 nm Methods: Whole heparinized blood was diluted with plasmalyte to 50% in the presence or absence of NM3014. Samples were centrifuged, and plasma was subjected to hemolysis assay. Plasma final concentration as 10% in GVB (GVB containing 10 mM MgCl2, 5 mM EGTA). rRBC was added and hemolysis of all samples were recorded. As expected NM3014 inhibits complement activity in human plasma. These data compare well with the sC5b-9 ELISA shown in FIG. 10.

Figure 10B:
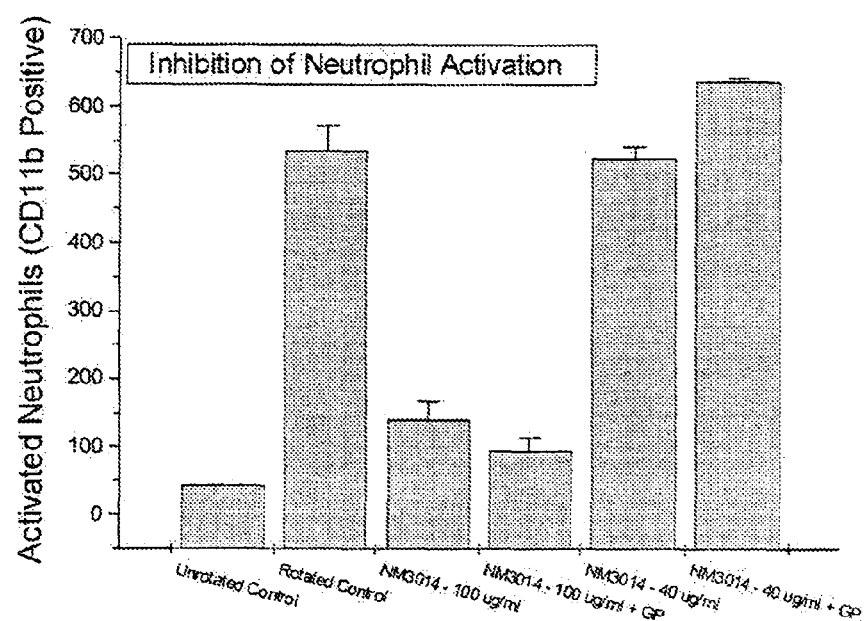

FIG. 10b illustrates NM3014 Inhibits Neutrophil Activation: In an Extra Corporeal Circulation Model, we showed that NM3014 at 100 µg/ml inhibits complement activity in whole blood. We also demonstrated that NM3014 at 40 µg/ml in whole blood does not inhibit complement activity. Same samples of blood following the tubing loop were also subjected to neutrophil specific flow cytometry. The data shows that NM3014 prevents neutrophil activation while a concentration of 40 µg/ml has no effect. These results mirror the results obtained for complement activity. Blood samples treated with NM3014 plus anti-GPIIbIIIa monoclonal (GP) did not help inhibition or activation of neutrophils. Similar data was obtained with multiple donors. In the Figure are shown Rotated Control (blood sample in tubing loop), Unrotated controls (samples taken out before tubing loop). Unrotated represents the background controls.

Figure 10C:
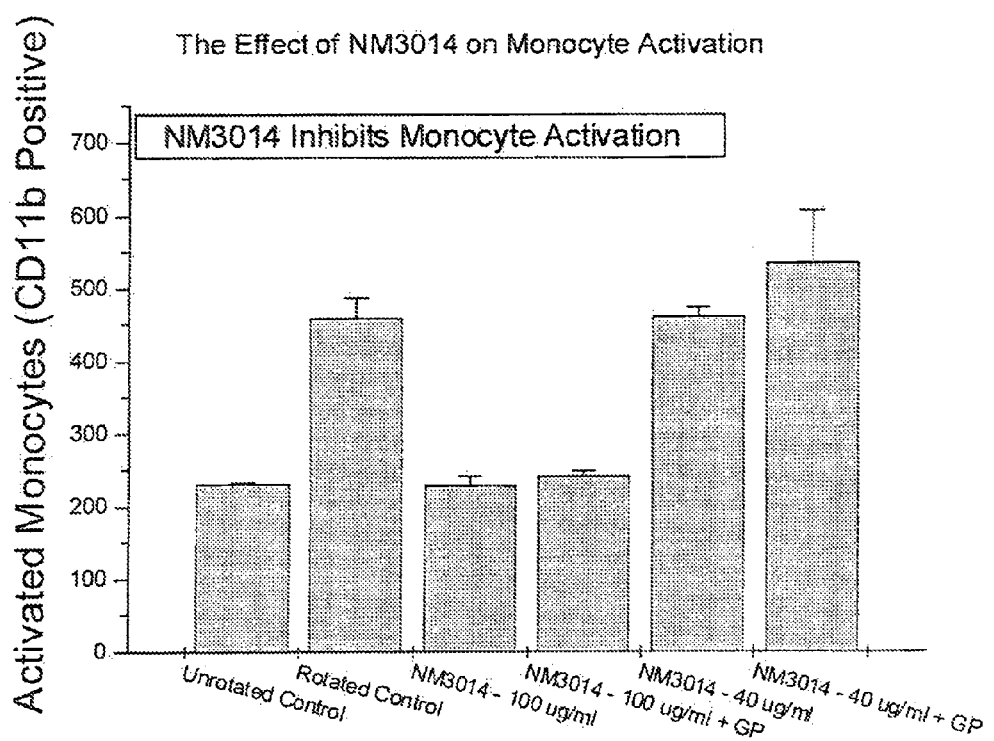

FIG. 10c illustrates NM3014 Inhibits Monocyte Activation: In an Extra Corporeal Circulation Model, we showed that NM3014 at 100 µg/ml inhibits complement activity in whole blood. We also demonstrated that NM3014 at 40 µg/ml in whole blood does not inhibit complement activity. Same samples of blood following the tubing loop were also subjected to monocyte specific flow cytometry. The data shows that NM3014 prevents monocyte activation while a concentration of 40 µg/ml has no effect. These results mirror the results obtained for complement activity and inhibition of neutrophil activation. Blood samples treated with NM3014 plus anti-GPIIbIIIa monoclonal (GP) did not help inhibition or activation of neutrophils. Similar data was obtained with multiple donors. In the Figure are shown Rotated Control (blood sample in tubing loop), Unrotated controls (samples taken out before tubing loop). Unrotated represents the background controls.

Figure 10D:
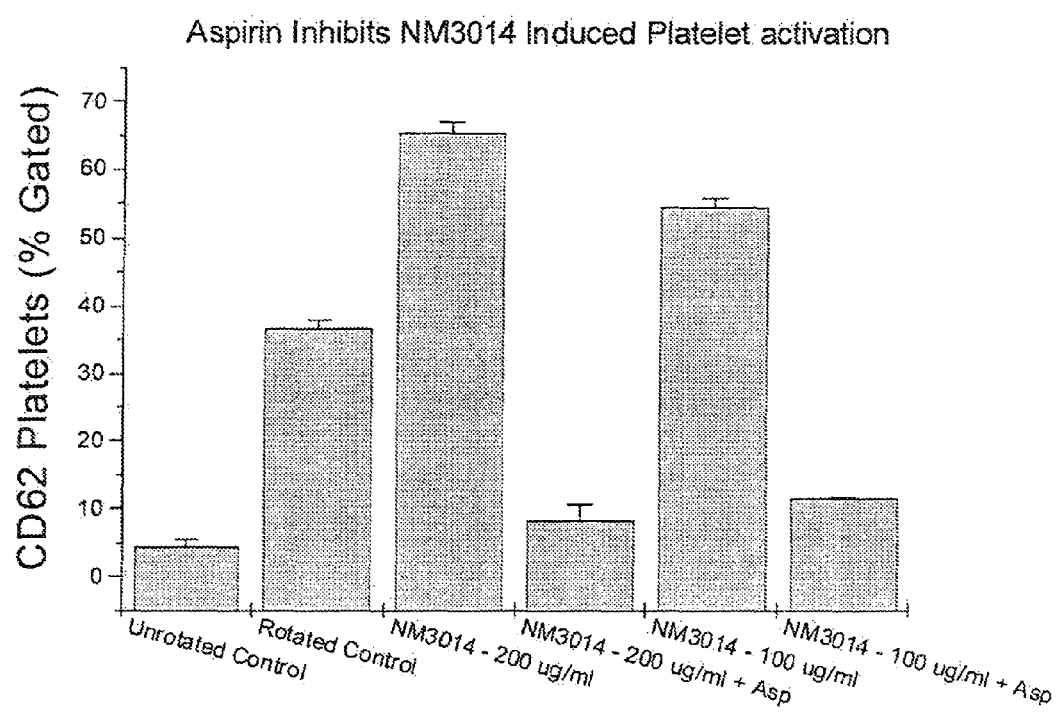

FIG. 10d illustrates Aspirin Inhibits NM3014 Induced Platelet Activation: NM3014 (Dextran Sulfate mw 40,000) activates platelet at both concentrations (100 µg/ml and 40 µg/ml) above the control levels. NM3014 in FIG. 10 shows inhibition of complement activity at 100 µg/ml. It was expected that platelet activation would also be inhibited. These data do not mirror the results obtained for neutrophils, monocytes and sC5b-9 shown in FIGS. 10, 10b, and 10c. As shown, addition of neutralizing Aspirin (100 µg/ml) to NM3014 prior to tubing loop rotation not only prevented platelet activation, but caused inhibition of platelet activation much below the control levels making this data of great significance for combination therapy. The inhibition of platelet activation was measured using flow cytometry following CD62P staining of activated platelets. These studies have been repeated with multiple donors with similar results.

Figure 10E:
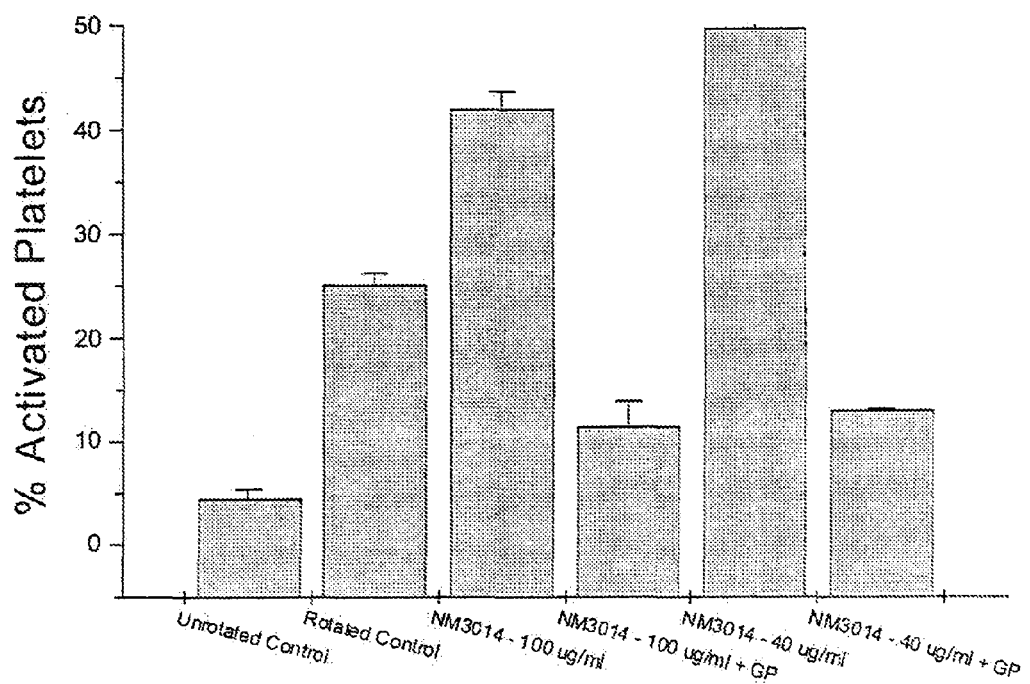

FIG. 10e illustrates Anti-GPIIbIIIa Inhibits NM3014 Induced Activation of Platelets: NM3014 (Dextran Sulfate mw 40,000) activates platelet at both concentrations (100 µg/ml and 40 µg/ml). NM3014 in FIG. 10 shows inhibition of complement activity at 100 µg/ml. It was expected that platelet activation will also be inhibited. These data does not mirror the results obtained for neutrophils, monocytes and sC5b-9 shown in FIGS. 10, 10b, and 10c. As shown, addition of neutralizing anti-GPIIbIIIa monoclonal antibody (10 µg/ml) to NM3014 not only prevented platelet activation, but caused inhibition of platelet activation much below control levels making this data of great significance as it relates to the use of NM3014 as a potent therapeutic. The inhibition of platelet activation was measured using flow cytometry following CD62P staining of activated platelets. These studies have been repeated with multiple donors with similar results.

DETAILED DESCRIPTION

The present invention relates to the use of Dextran Sulfate alone or in combination with an antiplatelet agent to inhibit in a subject complement activation, thrombin generation, and platelet aggregation in a subject with minimized or reduced hemorrhagic properties and high selectivity for surface-bound thrombin inhibition.

Dextran Sulfate, a carbohydrate polymer, has been a subject of study for almost two decades. Previous studies have shown that Dextran Sulfate can activate the alternative pathway by virtue of its C3 activating properties. In contrast, it was found that Dextran Sulfate inhibits the lysis of rabbit erythrocyte in buffer that allows alternative complement pathway activation to proceed and inhibits the formation of C5b-9/sC5b-9 on LPS coated plates under conditions that allow alternative pathway activation. Rabbit erythrocytes are known to activate the alternative pathway in human serum in alternative pathway specific buffer. Our results further demonstrate that Dextran Sulfate binds properdin in blood and as a result, blocks its association with C3b. Properdin plays a role in the regulation of the alternative pathway by virtue of its ability to bind and stabilize the inherently labile C3 and C5 convertase complexes (C3bBb and C3bBbC3b). This is despite the exact mechanism of C3 convertase stabilization being unknown.

The Dextran Sulfate mediated inhibition of the alternative pathway, as shown by the rabbit erythrocyte lysis and LPS-dependent C5b-9 assay, is associated with the inhibition of complement activation via the alternative pathway. As shown in detail in the Examples, Dextran Sulfate not only inhibited C5b-9 formation but also blocked formation of products of the alternative pathway, including C3a and C5a. Thus, Dextran Sulfate polymers can be used for inhibition of alternative pathway (AP) complement activation and can be used to treat clinical conditions where AP activation plays an important role in disease pathology (e.g., ischemic reperfusion injuries and cardiopulmonary bypass).

One aspect of the present invention, therefore, relates to a method administering Dextran Sulfate to a subject to inhibit the complement cascade and to treat clinical conditions associated with complement activation products and/or activation of the complement pathway (e.g., alternative complement pathway), such as thromboembolic disorders. The following definitions are provided in order to provide clarity with respect to the terms as they are used in the specification and claims, in order to describe the present invention.

As used herein, the term "alternative pathway" refers to complement activation, which has traditionally been thought to arise from spontaneous proteolytic generation of C3b from complement factor C3 triggered, for example, by zymosan from fungal and yeast cell walls, lipopolysaccharide (LPS) from Gram-negative outer membranes, and rabbit erythrocytes, as well as from many pure polysaccharides, rabbit erythrocytes, viruses, bacteria, animal tumor cells, parasites and damaged cells. The alternative pathway can also provide an amplification loop for complement activation initially triggered via the classical and lectin pathways, in addition to its widely accepted role as an independent pathway for complement activation. In this alternative pathway-mediated amplification mechanism, the activation generated C3 convertase (C4b2b) from either the classical or the lectin complement cascades cleaves C3 into C3a and C3b, and thereby provides C3b that can participate in forming C3bBb, the alternative pathway C3 convertase.

As used herein, the term "classical pathway" refers to complement activation of the C1-complex triggered by an antibody bound to a foreign particle and requires binding of the recognition molecule C1q. As used herein, the term "classical pathway" refers to complement activation that occurs via antigen-antibody complex formation, and the term lectin pathway refers to complement activation that occurs via the specific binding of serum and non-serum carbohydrate-binding proteins including mannan-binding lectin (MBL) and the ficolins.

As used herein, the term "AP inhibitory agent" refers to any agent that binds to a complement protein and effectively inhibits AP dependent complement activation, including Dextran Sulfates of varying molecular weights with varying degree of sulfation. Such AP inhibitory agents are useful in the method of the invention and will reduce AP-dependent complement activation.

As used herein, the "membrane attack complex" ("MAC") refers to a complex of the five terminal complement components (C5-C9) that inserts into and disrupts membranes also referred to as C5b-9.

As used herein, "a subject" includes all mammals, including without limitation dogs, cats, horses, sheep, goats, cows, rabbits, pigs, humans, non-human primates, and rodents.

The Dextran Sulfate in accordance with the present invention can have a molecular weight of greater than about 400 Daltons and a sulfur content of at least about 10%, by weight. In one example, the Dextran Sulfate can have a molecular weight of about 1000 Daltons to about 500,000 Daltons and a sulfate content of about 12% to about 18%, by weight.

Dextran Sulfate can be administered to a subject with a clinical condition (e.g., AP-dependent complement mediated disorder or disease) associated with complement activation in an amount effective to inhibit C3b-dependent complement activation in the subject. In the practice of this aspect of the invention, Dextran Sulfate of varying molecular weight and sulfation that prevent binding of properdin to C3b, and prevent production of C3a, C5a and C5b-9 by inhibition of the C3 cleavage into C3b can be administered to the subject.

The Dextran Sulfates can be administered to the subject as a primary therapy to treat a complement mediated clinical condition in the subject or in combination with an agent the inhibits platelet activation and/or platelet aggregation (i.e., an antiplatelet agent). Administration of the Dextran Sulfate in combination with the antiplatelet agent can be done in a combined dose or as separate related doses and with the intention to prevent and/or treat a variety of complement-mediated disorders, such as thromboembolic disorders. It is proposed that the administration of a combined therapeutically effective amount of a Dextran Sulfate with thrombin inhibitory properties and molecules that prevent platelet activation and/or platelet aggregation can provide a superior therapeutic effect in numerous areas. These surprising therapeutic benefits can be achieved while creating reduced risk of hemorrhagic side effects, such as prolonged bleeding.

In one example, the antiplatelet agent can include a COX inhibitor, such as aspirin and aspirin-like drugs. The enzymatic activity of cyclooxygenase (COX) is blocked by aspirin. After aspirin ingestion, a serine residue of COX becomes acetylated by the acetyl portion of the aspirin molecule. The effectiveness of aspirin appears to be dependent on its ability to block the formation of thromboxane A2 irreversibly by blocking the COX activity of the PGG/H synthetase system. Two isoforms of COX exist. Cyclooxygenase-1 (COX-1) in platelets leads to thromboxane A2 production and causes platelet aggregation, whereas COX-2 is induced by inflammatory stimuli. Aspirin inhibits COX-2 at higher concentrations than those required to inhibit COX-1. This may account, in part, for the different dose requirements of analgesic and anti-inflammatory versus antiplatelet effects of the drug.

In another example, the antiplatelet agent can include ticlopidine and/or clopidogrel. Ticlopidine (marketed as Ticlid by Roche US Pharmaceuticals) has a proposed mechanism of action that interferes selectively with ADP-induced transformation of GPIIb/IIIa complex expression in activated platelets. Ticlopidine is used especially in patients where aspirin is not tolerated. It also inhibits platelet aggregation induced by thrombin, collagen, arachidonic acid, and platelet-activating factor. Ticlopidine administered in a dose of 250 mg, twice daily, reduced the incidence of a combined endpoint of stroke, myocardial infarction, or vascular death by roughly 30%. Due to the increased risk of thrombotic thrombocytopenic pupura (TTP) and neutropenia, Ticlopidine was replaced by the newer drug Clopidogrel. Clopidogrel (marketed as Plavix—Bristol Myers) is another ADP antagonist that inhibits the binding of fibrinogen to its platelet receptor, the GPIIb/IIIa integrin. It does not directly modify the GPIIb/IIIa complex, suggesting that Clopidogrel acts indirectly to reduce fibrinogen binding. In healthy volunteers, it inhibited ADP and thrombin-induced platelet aggregation. The drug selectively reduced the number of functional ADP receptors mediating the inhibition of stimulated adenylate cyclase. Clopidogrel-induced platelet inhibition persists several days after withdrawal of the drug and diminishes in proportion to platelet renewal. Clopidogrel is administered as 75 mg tablets daily. The clinical studies of PLAVIX comes from four double-blind trials involving 81,090 patients: the CAPRIE study the CURE studies where they compared PLAVIX to placebo, both given in combination with aspirin and other standard therapy and CLARITY-TIMI 28 (Clopidogrel as Adjunctive Reperfusion Therapy—Thrombolysis in Myocardial Infarction). In comparison with Ticlopidine, Clopidogrel is more potent, and neutropenia has not been demonstrated. Clopidogrel is significantly more active than aspirin.

In yet another example, the antiplatelet agent can include a GPIIb/IIIa inhibitor. Glycoprotein IIb/IIIa receptor is expressed following agonist stimulation. This receptor binds with multiple adhesive ligand molecules, including fibrinogen, vWF (in conditions of high shear as might exist in stenotic arteries), fibronectin, vitronectin, and thrombospondin, which causes platelets to aggregate. Platelet recruitment is inhibited by anti-GPIIb/IIIa agents, such as monoclonal antibodies (c7E—ReoPro), cyclic peptide sequences (Eptifibatide—Integrilin), and by synthetic competitive analogues (Tirofiban—Aggrastat) Calvete, J. J., Platelet integrin GPIIb/IIIa: structure-function correlations. An update and lessons from other integrins. Proceedings of the Society for Experimental Biology and Medicine, 1999. 222(1): p. 29; Gabriel, H. M. and E. I. Oliveira, Role of abciximab in the treatment of coronary artery disease. Expert Opinion on Biological Therapy, 2006. 6(9): p. 935; Lal, H., et al., Integrins: novel therapeutic targets for cardiovascular diseases. Cardiovascular & Hematological Agents in Medicinal Chemistry, 2007. 5(2): p. 109; Menozzi, A., P. A. Merlini, and D. Ardissino, Tirofiban in acute coronary syndromes. Expert Review of Cardiovascular Therapy, 2005. 3(2): p. 193; Ringleb, P. A., Thrombolytics, anticoagulants, and antiplatelet agents. Stroke, 2006. 37(2): p. 312). The monoclonal antibody c7E3 (Abciximab or ReoPro produced by Centocor) inhibits the GPIIb/IIIa receptor, has undergone extensive clinical trials and received approval for clinical use. It has been shown to prevent thrombus formation after vascular injury and to be effective in reducing early reocclusion following coronary interventional procedures (Expert Opinion on Biological Therapy, 2006. 6(9): p. 935) Abciximab is a popular drug at BUMC and ranks in the top in annual pharmaceutical expenditures (The Baylor Drug Newsletter, June 1998; 10 (Crit Rev Immunol, 1981. 1(4): p. 321-66)). Striking inhibition of platelet hemostatic functions and substantial bleeding at intervention sites can occur, but complications were low in the Epilogue Stent Trial. Thrombocytopenia has been observed but is a rare occurrence (Schafer, A. I., Antiplatelet therapy with glycoprotein IIb/IIIa receptor inhibitors and other novel agents. Tex Heart Inst J, 1997. 24(2): p. 90-6). The plasma half-life of Abciximab is short in plasma but the antibody can bind to the GPIIb/IIIa receptor for long periods of time after termination of treatment. Patients undergoing Abciximab treatment can suffer from increased risk of bleeding and gastrointestinal hemorrhage Nonpeptide antagonists that mimic the charge and geometric characteristics of the arginine-glycine-aspartic acid sequence have been developed. These agents have the potential to be orally administered and, thus, effective for chronic antiplatelet therapy. Tirofiban (marketed as Aggrastat by MERCK), received new drug approval in May 1998 for clinical use. Clinical studies involving 7300 patients with non-Q-wave myocardial infarction revealed prevention of myocardial infarction occurrence for 6 months when Tirofiban was combined with heparin and aspirin therapy. Tirofiban is administered intravenously at 0.4 µg/kg per minute for 30 minutes initially and then reduced to 0.1 µg/kg per minute constant infusion. Intravenous administration of Tirofiban in conjunction with heparin and aspirin functions as a reversible antagonist to fibrinogen binding to the GPIIb/IIIa receptor, thus preventing the formation of platelet-platelet aggregates, which in turn prevents thrombus formation. The benefit of this drug is the clearance rate and half-life of the chemical, which prevents long-term platelet damage to the patients undergoing treatment.

Naturally occurring GPIIb/IIIa-antagonist peptides have been discovered and characterized in vitro and in vivo as Eptifibatide (Integrilin—Millennium Pharmaceuticals). Eptifibatide is a cyclic heptapeptide with a lysine-glycine-aspartic acid sequence rather than an arginine-glycine-aspartic acid sequence. The substitution of lysine for arginine makes this agent specific for the GPIIb/IIIa receptor. The PURSUIT trial confirmed that in patients with unstable angina or non-Q-wave myocardial infarction, Eptifibatide injection reduces the combined incidence of death or myocardial infarction, regardless of patient management strategy. Eptifibatide became available in June 1998 and is as gaining popularity over Abciximab due to its irreversible binding properties. Eptifibatide is used in conjunction with aspirin, Clopidogrel, and heparin. The dosage of Eptifibatide is an intravenous loading dose of 180 µg/kg over 1 to 2 minutes immediately after diagnosis, followed by continuous intravenous infusion of 2 µg/kg per minute until termination of treatment or initiation of coronary artery bypass grafting, or for up to 72 hours.

The Dextran Sulfate and/or the antiplatelet agent can be provided in a pharmaceutical composition or in separate compositions. Such pharmaceutical compositions can include therapeutically effective amount of a Dextran Sulfate (and antiplatelet agent) formulated in combination with one or more non-toxic pharmaceutically acceptable carriers. As used herein, the term "pharmaceutically acceptable carrier" means a non-toxic, insert solid, semi-solid or liquid filler, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention can be administered to humans and other animals orally, rectally, parenterally, intracisternally, intravaginally, intraperitoneally, transdermally, topically (as by powders, ointments, or drops), bucally, or as an oral or nasal spray.

Liquid dosage forms for oral administration include pharmaceutically acceptable emulsions, micro emulsions, solutions, suspensions, syrups, and elixirs. In addition to the active compounds, the liquid dosage forms may contain inert diluents commonly used in the art, for example, water or other solvents, solubilizing agents and emulsifiers. Others include items such as ethyl alcohol, isopropyl alcohol, ethyl carbonate, ethyl acetate, benzyl alcohol, benzyl benzoate, propylene glycol, 1,3-butylene glycol, dimethylformamide, oils, (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral composition can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluents or solvent, for example, as a solution in 1,3-butanediol. Among the acceptable vehicles and solvents that may be employed are water, Ringer's solution, U.S.P., and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in preparation of injectables.

The injectables formulations can be sterilized, for example, by filtration through a bacterial-retaining filter, or by incorporating sterilizing agents in the form of sterile solid compositions, which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which in turn, may depend upon crystal size and crystalline form. Alternatively, delayed absorption of a parenterally administered drug is accomplished by dissolving or suspending the drug in an oil vehicle. Injection depot forms are made by forming micorencapsule matrices of the drug in biodegradable polymers such as polylactide-polylactide-polyglycolide. Depending upon the ratio of drug to polymer and the nature of the particular polymer employed, the rate of drug release can be controlled. Examples of other biodegradable polymers include poly (orthoesters) and poly (anhydrides) Depot injectable formulations are also prepared by entrapping the drug in liposomes of micro emulsions, which are compatible with body tissues.

Compositions for rectal or vaginal administration are preferably suppositories, which can be prepared by mixing the compounds of this invention with suitable non-irritating excipients or carriers. These can include cocoa butter, polyethylene glycol or a suppository wax which are solid at ambient temperature but liquid at body temperature and therefore melt in the rectum or vaginal cavity and release the active compound. Solid compositions of a similar type may be employed as fillers in soft and hard-filled gelatin capsules using such excipients as lactose or milk sugar as well as high molecular weight polyethylene glycols and the like.

The active compounds can also be in microencapsulated form with one or more excipients as noted above. The solid dosage forms of tablets, dragees, capsules, pills, and granules can be prepared with coatings and shells such as enteric coatings, release-controlling coatings well known in the pharmaceutical formulating art. In such solid dosage forms, the active compound may be admixed with at least one inert diluent, such as sucrose, lactose, or starch. Such dosage forms may also comprise, as is normal practice, additional substances other inert diluents, e.g., tableting lubricants and other tableting acids such as magnesium stearate and microcrystalline cellulose. In the case of capsules, tablets and pills, the dosage forms may also comprise buffering agents. They may optionally contain opacifying agents and be also of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is mixed under sterile conditions with a pharmaceutically acceptable carrier and any needed preservatives or buffers as may be required. Ophthalmic formulation, eardrops, eye ointments, powders, and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicaters and polyamide powder, or mixtures of these substances. Sprays can additionally contain customary propellants such as chlorofluorohydrocarbons.

Transdermal patches have the added advantages of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

Complement Mediated Clinical Conditions

Complement mediated clinical conditions that can be treated by administration of the Dextran Sulfate alone or in combination with the antiplatelet agent can include any condition, disorder, and disease as well as complication from medical procedures in which the complement system has been implicated as contributing to the pathogenesis. While complement may not be the only cause of the pathogenesis in these conditions, it is nevertheless a major pathological mechanism and represents an effective point for clinical control in many of these disease states.

Complement activation products have been detected in biological fluids or diseased tissues isolated from patients, and a correlation between the severity of the clinical indication with the abundance of complement activation products has been demonstrated for some diseases. The most compelling evidence directly implicating complement in the pathogenesis of a diverse group of human diseases comes from studies using animal models of such diseases. In such animal models depletion of complement by cobra venom factor inhibition of complement activity or testing in animals genetically deficient in specific complement components have all been shown to abrogate or delay pathogenesis.

Ischemia Reperfusion Injury

The complement mediated clinical condition can include ischemia reperfusion injury (I/R) tissue damage that occurs when blood supply returns to the tissue after an extended period of ischemia. I/R is a common source of morbidity and mortality in a wide spectrum of diseases. Patients are vulnerable to I/R after surgery such as cardiopulmonary bypass, aortic aneurysm repair, vascular reanastomosis in connection with, for example, organ transplants (e.g., heart, lung, liver, and kidney) and digit/extremity replantation, stroke, myocardial infarction and hemodynamic resuscitation following shock and/or surgical procedures. Patients with atherosclerotic diseases are prone to strokes, myocardial infarctions, and emboli-induced intestinal and lower-extremity ischemia and those who experience trauma, frequently suffer from temporary ischemia of the limbs. Additionally any case of large amounts of blood loss can lead to a severe whole-body I/R reaction. The pathophysiology of I/R injury is complex, with at least two major factors contributing to the process: complement activation and neutrophil stimulation with accompanying oxygen radical-mediated injury.

The membrane attack complex is the most significant vehicle of complement-directed injury and studies in animals with a C5-deficiency have shown decreased local and remote injury in models of I/R injury. An inhibitor of complement activation, soluble Crry (complement receptor-related gene Y), has shown effectiveness against injury when given both before and after the onset of murine intestinal reperfusion. In a model of skeletal muscle ischemia, the use of soluble complement receptor 1 (sCR1) also reduced muscle injury when given after the start of reperfusion. In a porcine model of myocardial I/R, animals treated with monoclonal antibody ("MoAb") to the anaphylatoxin C5a prior to reperfusion showed attenuated infarction. Rats treated with C5 MoAb demonstrated attenuated infarct size, neutrophil infiltration, and apoptosis in the myocardium.

The results of these experiments illustrate the importance of complement activation in the development of I/R injury. However, it is not specifically clear which complement pathway (classical, lectin or alternative) is predominantly involved in complement activation during cases of I/R injury.

One aspect of the invention is thus directed to the treatment of ischemia reperfusion injuries by treating a subject experiencing ischemic reperfusion with a therapeutically effective amount of Dextran Sulfate (alone or in combination with an antiplatelet agent) commencing immediately after or as soon as possible after an ischemia reperfusion event. In instances where reperfusion occurs in a controlled environment (e.g., following an aortic aneurism repair, organ transplant or reattachment of severed or traumatized limbs or digits), the Dextran Sulfate (alone or in combination with an antiplatelet agent) may be administered prior to and/or during and/or after reperfusion. The Dextran Sulfate (alone or in combination with an antiplatelet agent) can be administered in various ways by intra-arterial, intracranial, intravenous, subcutaneous, intramuscular, or other parenteral administration. Potentially orally for non-peptidergic inhibitors, and most suitably by intra-arterial or intravenous administration. Administration may be repeated periodically as determined by a physician for optimal therapeutic effect.

Atherosclerosis

There is considerable evidence that complement activation is involved in atherogenesis in humans. Components of the terminal complement pathway are frequently found in human atheromas. C3 and C4 deposition in arterial lesions has also been demonstrated. The extent of C5b-9 deposition was found to correlate with the severity of the lesion. In ruptured and vulnerable plaques, deposition of complement iC3b, but not C5b-9, was especially strong, suggesting that complement activation may be a factor in acute coronary syndromes. In experimental atheroma in rabbits, complement activation was found to precede the development of lesions.

Other Vascular Diseases and Conditions

Complement-mediated vascular injury has been shown to contribute to the pathophysiology of several diseases of the cardiovascular system, including atherosclerosis, ischemia-reperfusion injury, and myocardial infarction. Evidence suggests that complement activation may extend to other vascular conditions, for example, pathogenesis of many forms of vasculitis, including: Henoch-Schonlein purpura nephritis, immune complex vasculitis, vasculitis associated with rheumatoid arthritis (also called malignant rheumatoid arthritis), systemic lupus erythematosus-associated vasculitis, and Takayasu's disease.

Frequently associated with severe vasculitis, systemic lupus erythematosus (SLE) is an example of systemic autoimmune diseases that affects multiple organs including skin, kidneys, joints, serosal surfaces, and central nervous system. IgG anti-endothelial antibodies and IgG complexes capable of binding to endothelial cells are present in the sera of patients with active SLE, and deposits of IgG immune complexes and complement are found in blood vessel walls of patients with SLE vasculitis. Another pleomorphic group of human diseases in which complement-dependent cytotoxicity against endothelial and other cell types plays a documented role includes such diseases as rheumatoid arthritis associated with vasculitis, also called malignant rheumatoid arthritis, immune-complex vasculitis, leukocytoclastic vasculitis, vasculitis associated with hepatitis A, and the arteritis known as Takayasu's disease.

Other evidence has suggested that complement activation plays a role in dilated cardiomyopathy, characterized by impaired systolic function of the heart and cardiac enlargement. Recent data suggests that ongoing inflammation in the myocardium may contribute to the development of disease. Strong correlation has been identified between C5b-9, the terminal membrane attack complex of complement activation, and immunoglobulin deposition and myocardial expression of TNF-alpha. Suggesting that chronic immunoglobulin-mediated complement activation in the myocardium may contribute in part to the progression of dilated cardiomyopathy, myocardial accumulation of C5b-9 was demonstrated in myocardial biopsies from 28 patients with dilated cardiomyopathy.

One aspect of the invention is thus directed to the treatment of a vascular condition, including peripheral vascular conditions, renovascular conditions, cardiovascular conditions, cerebrovascular conditions, and mesenteric/enteric vascular conditions, by administration of a composition comprising a therapeutically effective amount of a Dextran Sulfate (alone or in combination with an antiplatelet agent). Examples of conditions for the current invention include, without limitation: vasculitis, including Henoch-Schonlein purpura nephritis, vasculitis associated with rheumatoid arthritis (also called malignant rheumatoid arthritis), immune complex vasculitis, systemic lupus erythematosus-associated vasculitis, and Takayasu's disease, dilated cardiomyopathy; diabetic angiopathy; Kawasaki's disease (arteritis); and venous gas embolus (VGE).

Gastrointestinal Disorders

Inflammatory bowel disease (IBD) includes chronic inflammatory disorders of the bowel that include ulcerative colitis and Crohn's disease, often characterized by spontaneously occurring, chronic, relapsing inflammation of unknown origin. The activation of the complement system in patients with IBD is thought to play a role in disease pathogenesis. It has been shown that C3b and other activated complement products are found at the luminal face of surface epithelial cells, in the muscularis mucosa as well as the sub mucosal blood vessels in IBD patients.

Another aspect of the invention is thus directed to the treatment of a subject with IBD by administering to the subject a composition comprising a therapeutically effective amount of a Dextran Sulfate (alone or in combination with an antiplatelet agent).

Pulmonary Conditions

Complement activation has been implicated in the pathogenesis of many lung inflammatory disorders including: asthma; Wegener's granulomatosis; chronic obstructive pulmonary disease (COPD); acute respiratory distress syndrome (ARDS); transfusion-related acute lung injury (TRALI); ischemia/reperfusion acute lung injury; and antiglomerular basement membrane disease (Goodpasture's disease). It is now well accepted that much of the pathophysiology of ARDS involves a dysregulated inflammatory cascade that begins as a normal response to an infection or other inciting event, but ultimately causes significant auto injury to the host. Patients with ARDS almost universally show evidence of extensive complement activation such as increased plasma levels of complement components C3a and C5a. The degree of complement activation has been correlated with the development and outcome of ARDS. Asthma is essentially an inflammatory disease and evidence that the complement system is highly active in the human asthmatic lung is well documented. Recent data from animal models and humans provide evidence that complement activation is a significant mechanism contributing to disease pathogenesis.

Experimental and clinical data suggests a role for complement activation in the pathophysiology of ARDS. Various animal models have illustrated that systemic activation of complement leads to acute lung injury with histopathology similar to that seen in human ARDS Inhibiting the complement biochemical cascade by general complement depletion or by specific inhibition of C5a provides protection in animal models of acute lung injury.

Another aspect of the invention is thus directed to the treatment of a subject with a lung inflammatory disorder including but not limited to asthma; Wegener's granulomatosis; chronic obstructive pulmonary disease (COPD); acute respiratory distress syndrome (ARDS); transfusion-related acute lung injury (TRALI); ischemia/reperfusion acute lung injury; and antiglomerular basement membrane disease (Goodpasture's disease) by administering to the subject a composition comprising a therapeutically effective amount of a Dextran Sulfate (alone or in combination with an antiplatelet agent).

Extracorporeal Circulation

Various medical procedures divert blood from a patient's circulatory system known as extracorporeal circulation systems (ECC). Some of these procedures include hemodialysis, leukopheresis, plasmapheresis, heparin-induced extracorporeal membrane oxygenation LDL precipitation (HELP), extracorporeal membrane oxygenator (ECMO), and cardiopulmonary bypass (CPB). These procedures involve the exposure of blood products or blood to foreign surfaces that have the capacity to alter normal cellular function and hemostasis. Studies have identified complement activation as the probable cause of granulocytopenia during hemodialysis. Indications that activation of the complement system caused many of the adverse events experienced by patients undergoing hemodialysis or CPB have been identified in recent studies. For example, the potential of complement system activation has been shown to be an important criterion in determination of the biocompatibility of hemodialyzers with respect to recovery of renal function, susceptibility to infection, pulmonary dysfunction, morbidity, and survival rate of patients with renal failure.

Partly caused by exposure of blood to artificial surfaces as well as surface-independent factors like surgical trauma and ischemia-reperfusion injury, patients undergoing ECC during CPB suffer a systemic inflammatory reaction. The CPB-triggered inflammatory reaction can result in post surgical complications, generally termed "post perfusion syndrome". Included in postoperative events are cognitive deficits, bleeding disorders, respiratory failure, renal dysfunction and, in the most severe cases, multiple organ failure. Coronary bypass surgery with CPB leads to profound activation of the complement system, in contrast to surgery with a comparable degree of surgical trauma but without CPB. Therefore, the primary suspected cause of these CPB-related problems is inappropriate activation of complement during the bypass procedure. In CPB circuits, the alternative complement pathway plays a predominant role in complement activation because of the exposure of blood with artificial surfaces within the CPB circuits. However, there is also evidence that the classical complement pathway is activated during CPB.

Following activation of the complement system, primary inflammatory substances are generated including anaphylatoxins C3a and C5a, the opsonin C3b, as well as the membrane attack complex C5b-9. C3a and C5a are potent stimulators of neutrophils, monocytes, and platelets release of pro-inflammatory cytokines (IL-1, IL-6, IL-8, and TNF alpha), oxidative free radicals and proteases results from the activation of the inflammatory substances. C5a has been shown to upregulate adhesion molecules CD11b and CD18 of Mac-1 in polymorphonuclear cells (PMNs), as well as induce degranulation of PMNs releasing pro-inflammatory enzymes. C5b-9 induces the expression of adhesion molecule P-selectin (CD62P) on platelets, whereas both C5a and C5b-9 induce surface expression of P-selectin on endothelial cells. These adhesion molecules are involved in the interaction among leukocytes, platelets, and endothelial cells, while their expression is responsible for sequestration of activated leukocytes mediating tissue inflammation and injury. It is the actions of these complement activation products on neutrophils, monocytes, platelets and other circulatory cells that likely lead to the various problems that arise after CPB.

Another aspect of the invention is thus directed to the treatment complement activation in a subject resulting from extracorporeal circulation procedure by administering to the subject a composition comprising a therapeutically effective amount of a Dextran Sulfate (alone or in combination with an antiplatelet agent).

Inflammatory and Non-Inflammatory Arthritides and Other Musculoskeletal Diseases Activation of the complement system has been implicated in the pathogenesis of a wide variety of rheumatological diseases; including rheumatoid arthritis, juvenile rheumatoid arthritis, and osteoarthritis, systemic lupus erythematosis (SLE), Behcet's syndrome and Sjogren's syndrome. There is compelling evidence that immune-complex-triggered complement activation is a major pathological mechanism that contributes to tissue damage in rheumatoid arthritis (RA). Documentation from numerous publications shows that complement activation products are elevated in the plasma of rheumatoid arthritis patients. Complement activation products such as C3a, C5a, and sC5b-9 have also been found within inflamed rheumatic joints and positive correlations have been established between the degree of complement activation and the severity of RA. Indications that complement activation is mediated predominantly by the alternative pathway include, in both adult and juvenile rheumatoid arthritis, elevated serum and synovial fluid levels of alternative pathway complement activation product Bb compared to C4d (a marker for classical pathway activation) through recruitment of inflammatory cells by the anaphylatoxins C3a and C5a or directly damage tissue (via C5b-9), complement activation products can indirectly mediate inflammation.

Systemic lupus erythematosus (SLE) is an autoimmune disease of undefined etiology that results in episodic, uncontrolled activation of the complement system, production of autoantibodies, and generation of circulating immune complexes. Although the origins of autoimmunity in SLE remain elusive, considerable information is now available implicating complement activation as an important mechanism contributing to vascular injury in this disease. Activation of both the classical and alternative pathways of complement is involved in the disease and both C4d and Bb are sensitive markers of moderate-to-severe lupus disease activity. Activation of the alternative complement pathway accompanies disease flares in systemic lupus erythematosus during pregnancy. Immune complex-mediated activation of complement through the classic pathway is believed to be one mechanism by which tissue injury occurs in SLE patients. Results from animal models of SLE support the important role of complement activation in pathogenesis of the disease. Inhibiting the activation of C5, using a blocking anti-C5 MoAb decreased proteinuria and renal disease in NZB/NZW F1 mice, a mouse model of SLE.

Another aspect of the invention is thus directed to the treatment of a subject with a rheumatological disorder and/or SLE by administering to the subject a composition comprising a therapeutically effective amount of a Dextran Sulfate (alone or in combination with an antiplatelet agent).

Renal Conditions

Activation of the complement system has been implicated in the pathogenesis of a wide variety of renal diseases; including, mesangioproliferative glomerulonephritis (IgA-nephropathy, Berger's disease), membranous glomerulonephritis, membranoproliferative glomerulonephritis (mesangiocapillary glomerulonephritis), acute postinfectious glomerulonephritis (poststreptococcal glomerulonephritis), cryoglobulinemic glomerulonephritis, lupus nephritis, and Henoch-Schonlein purpura nephritis. There continues to be a major discussion on complements exact role in the onset of renal disease despite acknowledgement of complement system involvement. Under normal conditions, the contribution of complement is beneficial to the host, but inappropriate activation and deposition may contribute to host cell and tissue damage. Substantial evidence exists that shows glomerulonephritis, inflammation of the glomeruli, is often initiated by deposition of immune complexes onto glomerular or tubular structures, triggering complement activation, inflammation, and tissue damage. Khan and Sinniah demonstrated increased deposition of C5b-9 in tubular basement membranes in biopsies taken from patients with various forms of glomerulonephritis (Khan, T. N. and R. Sinniah, Renal tubular antiproteinase (alpha-1-antitrypsin and alpha-1-antichymotrypsin) response in tubulo-interstitial damage. Nephron, 1993. 65(2): p. 232).

C5b-9 deposition in the tubular epithelial/basement membrane structures correlated with plasma creatinine levels in a study of patients with IgA nephrology. Another study of membranous nephropathy demonstrated a relationship between clinical outcome and urinary sC5b-9 levels. Elevated sC5b-9 levels were highly correlated with reduced prognosis. Lehto et al., measured, in urine from patients with membranous glomerulonephritis, elevated levels of a complement regulatory factor that inhibits the membrane attack complex in plasma membranes (CD59), as well as C5b-9. Deposition of C3 and C9 proteins in the glomeruli was revealed after histopathological analysis of biopsy samples taken from the same patients, whereas expression of CD59 in these tissues was diminished compared to that of normal kidney tissue. Ongoing complement-mediated glomerulonephritis results in urinary excretion of complement proteins correlating with the degree of tissue damage as well as disease prognosis, as suggested by these various studies.

In addition, demonstration of the importance of complement activation in the etiology of the disease was found in inhibition of complement activation during various animal models of glomerulonephritis. In a model of membranoproliferative glomerulonephritis (MPGN), infusion of anti-Thy1 antiserum in C6-deficient rats (that cannot form C5b-9) compared to C6+normal rats, resulted in 90% less glomerular cellular proliferation, 80% reduction in platelet and macrophage infiltration, diminished collagen type IV synthesis (a marker for mesangial matrix expansion), and 50% less proteinuria. These results implicate C5b-9 as a major mediator of tissue damage by complement activation.

In another model of glomerulonephritis, infusion of graded dosages of rabbit anti-rat glomerular basement membrane produced a dose-dependent influx of polymorphonuclear leukocytes (PMN) that was attenuated by prior treatment with cobra venom factor (to consume complement). Showing diminished histopathology, decreased long-term proteinuria, and lower creatinine levels, the cobra venom factor-treated rats differed from the control rats. Demonstrating the potential therapeutic efficacy of approaches to inhibit complement by using the recombinant sCR1 protein, Couser et al., employed three models of GN in rats (anti-thymocyte serum, Con A anti-Con A, and passive Heymann nephritis). Rats treated with sCR1 resulted in a significant reduction of PMN, platelet and macrophage influx, decreased mesangiolysis, and proteinuria versus control rats. Further evidence has been provided for the importance of complement activation in glomerulonephritis by the use of an anti-C5 MoAb in the NZB/W F1 mouse model. The anti-C5 MoAb inhibits cleavage of C5, therefore blocking the production of C5a and C5b-9. Continuous therapy with anti-C5 MoAb over the period of 6 months resulted in significant amelioration of the course of glomerulonephritis. A humanized anti-C5 MoAb monoclonal antibody (5G1.1) is under development by Alexion Pharmaceuticals, Inc., New Haven, Conn., that prevents the cleavage of human complement component C5 into its pro-inflammatory components. The antibody is considered a potential treatment for glomerulonephritis Direct evidence has been found by studies of patients with genetic deficiencies in specific complement components, for a pathological role of complement in renal injury. A number of reports have documented an association of deficiencies of complement regulatory factor H with renal disease. Factor H deficiency results in low plasma levels of factor B and C3 and in consumption of C5b-9 as well as an association with atypical membranoproliferative glomerulonephritis (MPGN) and idiopathic hemolytic uremic syndrome (HUS). Confirming the importance of factor H in complement regulation, factor H deficient pigs and factor H knockout mice display MPGN-like symptoms. Deficiencies of other complement components are associated with renal disease, secondary to the development of systemic lupus erythematosus (SLE). Through mechanisms relating to defective clearance of immune complexes and apoptotic material, deficiency for C1q, C4 and C2 predispose strongly to the development of SLE. In many of these SLE patients lupus nephritis occurs, which is characterized by the deposition of immune complexes throughout the glomerulus.

One aspect of the invention is thus directed to the treatment of renal conditions including but not limited to mesangioproliferative glomerulonephritis, membranous glomerulonephritis, lupus nephritis, membranoproliferative glomerulonephritis (mesangiocapillary glomerulonephritis), cryoglobulinemic glomerulonephritis, acute postinfectious glomerulonephritis (poststreptococcal glomerulonephritis), Henoch-Schonlein purpura nephritis, or IgA nephropathy by administering a therapeutically effective amount of Dextran Sulfate (alone or in combination with an antiplatelet agent) in a pharmaceutical carrier to a subject suffering from such a disorder. Such complement inhibitory agent may be administered to the subject systemically, such as by intramuscular, intra-arterial, intravenous, subcutaneous or other parenteral administration, or potentially by oral administration for non-peptidergic agents. The Dextran Sulfate may be administered periodically over an extended period of time for treatment or control of a chronic condition, or may be by single or repeated administration in the period before, during, or following acute trauma or injury.

Skin Disorders

Psoriasis is a chronic, debilitating skin condition affecting millions of people and has been attributed to both genetic and environmental factors. First-line of treatment for psoriasis generally includes topical agents as well as UVB and PUVA phototherapy. However, systemic therapy can be used as a primary treatment or used to augment UVB and PUVA therapy for generalized or more extensive disease. The underlying etiology of various skins diseases such as psoriasis supports a role for immune and pro-inflammatory processes including the involvement of the complement system. Often described as an immune-mediated disorder, it is thought that abnormal activity causes inflammation and cell growth activation. Moreover, the role of the complement system has been established as an important nonspecific skin defense mechanism. Its activation leads to the generation of products that aid in the maintenance of normal host defenses as well as mediate inflammation and tissue injury. Pro-inflammatory products of complement activation include large fragments of C3 with opsonic and cell-stimulatory activities (C3b and C3bi), low molecular weight anaphylatoxins (C3a, C4a, and C5a), and membrane attack complexes. Seemingly, the most important mediator is C5a or its degradation product C5a des Arg, because it exerts a potent chemotactic effect on inflammatory cells. Intradermal administration of C5a anaphylatoxin induces skin changes rather similar to those observed in cutaneous hypersensitivity vasculitis that occurs through immune complex-mediated complement activation.

Complement activation is involved in the pathogenesis of the inflammatory changes during autoimmune bullous dermatoses. Complement activation by pemphigus antibody in the epidermis seems to be responsible for the development of characteristic inflammatory changes termed eosinophilic spongiosis. In bullous pemphigoid (BP), seemingly related to leukocytes lining the dermoepidermal junction, interaction of basement membrane zone antigen and BP antibody leads to complement activation. The resulting anaphylatoxins activate the infiltrating leukocytes, as well as induce mast cell degranulation facilitating dermoepidermal separation and eosinophil infiltration. Similarly, complement activation seems to play a more direct role in the dermoepidermal separation noted in epidermolysis bullosa acquisita and herpes gestationis. Evidence for the involvement of complement in psoriasis comes from recent experimental findings described in the literature related to the pathophysiological mechanisms for the inflammatory changes in psoriasis and related diseases. The importance of T-cell-mediated immunity in the triggering and maintaining of psoriatic lesions is gathering support and further evidence. It has been revealed that lymphokines produced by activated T-cells in psoriatic lesions have a strong influence on the proliferation of the epidermis. Characteristic neutrophil accumulation under the stratum corneum can be observed in the highly inflamed areas of psoriatic lesions. Neutrophils are chemotactically attracted and activated there by synergistic action of chemokines, IL-8 and Gro-alpha released by stimulated keratinocytes, and particularly by C5a/C5a des-arg produced via the alternative complement pathway activation.

Psoriatic scale extracts contain two unrelated chemotactic peptides in this fraction, i.e., C5a/C5a des Arg and interleukin 8 (IL-8) and its related cytokines. Concentrations of C5a/C5a desArg and IL-8 in psoriatic lesional scale extracts and those from related sterile pustular dermatoses were quantified to investigate their relative contribution to the transepidermal leukocyte migration as well as their interrelationship in psoriatic lesions. It was found that the concentrations of C5a/C5a desArg and IL-8 were more significantly increased in the horny-tissue extracts from lesional skin than in those from non-inflammatory orthokeratotic skin. The increase of C5a/C5a desArg concentration was specific to the lesional scale extracts. Based on these results, it appears that C5a/C5a desArg is generated only in the inflammatory lesional skin, under specific circumstances that favor complement activation. This provides a rationale for the use of an inhibitor of complement activation to ameliorate psoriatic lesions. One study measured the levels of C4d and Bb in psoriatic scale extracts using enzyme immunoassay techniques. The scales of these dermatoses contained higher levels of C4d and Bb detectable by enzyme immunoassay than those in the stratum corneum of noninflammatory skin. These results suggest that the alternative pathway is activated in addition to the classical pathway of complement in psoriatic lesional skin. Additional evidence for the involvement of complement in psoriasis and atopic dermatitis has been obtained by measuring normal complement components and activation products in the peripheral blood of 35 patients with atopic dermatitis (AD) and 24 patients with psoriasis at a mild to intermediate stage. Levels of C3, C4 and C1 inactivator (C1 INA) were determined in serum by radial immunodiffusion, whereas C3a and C5a levels were measured by radioimmunoassay. The levels of C3, C4 and C1 INA were found to be significantly increased in both diseases in comparison to healthy non-atopic controls. In AD, there was a tendency towards increased C3a levels, whereas in psoriasis, C3a levels were significantly increased. The results indicate that, in both AD and psoriasis, the complement system participates in the inflammatory process.

By measuring levels of SC5b-9 in the plasma and horny tissues of psoriatic patients, complement activation in psoriatic lesional skin also results in the deposition of terminal complement complexes within the epidermis. The levels of SC5b-9 in psoriatic plasma have been found to be significantly higher than those of controls or those of patients with atopic dermatitis. Studies of total protein extracts from lesional skin have shown that, there were high levels of SC5b-9 in lesional horny tissues of psoriasis, despite no SC5b-9 detected in the noninflammatory horny tissues. By using a monoclonal antibody to the C5b-9 neoantigen in immunofluorescence, deposition of C5b-9 has been observed only in the stratum corneum of psoriatic skin. To summarize, psoriatic lesional skin shows complement system activation that proceeds all the way to the terminal step, leading to membrane attack complex.

One aspect of the invention is thus directed to the treatment of psoriasis, autoimmune bullous dermatoses, eosinophilic spongiosis, bullous pemphigoid, epidermolysis bullosa acquisita, atopic dermatitis, herpes gestationis and other skin disorders as well as for the treatment of thermal and chemical burns including capillary leakage caused thereby, by administering a composition comprising a therapeutically effective amount of a Dextran Sulfate (alone or in combination with an antiplatelet agent) to a subject suffering from such a skin disorder. The Dextran Sulfate may be administered to the subject topically, by application of a spray, lotion, gel, paste, salve or irrigation solution containing the Dextran Sulfate inhibitory agent, or systemically such as by intra-arterial, intravenous, intramuscular, subcutaneous or other parenteral administration, or potentially by oral administration for non-peptidergic inhibitors. Treatment may involve a single administration or if necessary repeated applications or dosing for an acute condition or by periodic applications or dosing for control of a chronic condition.

Transplantation

Inflammatory reaction after solid organ transplantation is due to significant contribution by the activation of the complement system. In allotransplantation, activation of the complement system may be caused by ischemia/reperfusion and possibly, antibodies directed against the graft. In xenotransplantation from nonprimates to primates, the major activators for the complement system are already existing antibodies. Studies in animal models have shown that the use of complement inhibitors may significantly prolong graft survival. Thus, establishing the role of the complement system in organ injury after organ transplantation. Therefore, the inventors believe by utilizing Dextran Sulfate damage prevention is possible in situation of grafts after allo- or xenotransplantation.

Innate immune mechanisms, particularly complement, play a greater role in inflammatory and immune responses against the graft than has been previously recognized. It appears that alternative complement pathway activation mediates renal ischemia/reperfusion injury, and in this setting proximal tubular cells may be both the source and the site of attack of complement components. Locally produced complement in the kidney also plays a role in the development of both cellular and antibody-mediated immune responses against the graft. C4d is the degradation product of the activated complement factor C4, a component of the classical and lectin-dependent pathways. The association between C4d and morphological signs of acute cellular rejection is statistically significant. C4d staining has emerged as a useful marker of humoral rejection both in the acute and in the chronic setting and led to renewed interest in the significance of anti-donor antibody formation. C4d is found in 24-43% of Type I episodes, in 45% of type II rejection and 50% of type III rejection. A number of therapies are in development that inhibit complement or reduce local synthesis as a means to achieve an improved clinical outcome following transplantation.

Complement plays a critical role in xenograft rejection, making effective complement inhibitors great targets as potential therapeutic agents. In pig-to-primate organ transplantation, hyperacute rejection (HAR) results from complement activation and antibody deposition. Multiple strategies and targets have been tested to prevent hyperacute xenograft rejection in the pig-to-primate combination. These approaches have been accomplished by removal of natural antibodies, complement depletion with cobra venom factor, or prevention of C3 activation with the soluble complement inhibitor sCR1. In addition, complement activation blocker-2 (CAB-2), a recombinant soluble chimeric protein derived from human decay accelerating factor (DAF) and membrane cofactor protein, inhibits C3 and C5 convertases of both classical and alternative pathways. A pig heart perfused ex vivo with human blood shows reduced complement-mediated tissue injury due to CAB-2. A study of the efficacy of CAB-2 including the transplantation of a pig heart into rhesus monkeys showed that graft survival was markedly prolonged in monkeys that received CAB-2 compared to those receiving no immunosuppression. CAB-2 markedly inhibited complement activation, as shown by a strong reduction in generation of C3a and SC5b-9. At graft rejection, tissue deposition of iC3b, C4 and C9 was similar or slightly reduced from controls, and deposition of IgG, IgM, C1q and fibrin did not change. Thus, this approach for complement inhibition abrogated hyperacute rejection of pig hearts transplanted into rhesus monkeys. These studies demonstrate the beneficial effects of complement inhibition on survival and the inventors believe that complement inhibition may also be useful in xenotransplantation.

The availability of specific inhibitors of complement may provide the opportunity for an improved clinical outcome following organ transplantation Inhibitors that act by a mechanism that blocks complement attack may be particularly useful, because they hold the promise of increased efficacy and avoidance of systemic complement depletion in an already immuno-compromised recipient.

Another approach has focused on determining if anti-complement C5 monoclonal antibodies could prevent hyperacute rejection (HAR) in a rat-to-presensitized mouse heart transplantation model. Also to determine if these MoAb, combined with cyclosporine and cyclophosphamide, could achieve long-term graft survival. Results found that anti-C5 MoAb prevents HAR, leading the inventors to believe that other targets in the complement cascade such as properdin, may also be valuable for preventing HAR and acute vascular rejection in future clinical cases of xenotransplantation. While the pivotal role of complement activation in hyperacute rejection seen in xenografts is well established, a more subtle role in allogeneic transplantation is beginning to be identified. A link between complement and the acquired immune response has long been known, with the finding that complement-depleted animals mounted subnormal antibody responses following antigenic stimulation. Impressive increases in effectiveness from opsonization of antigen with the complement split product C3d, has been shown on antigen presentation to B cells, and has been known to act via engagement of complement receptor type 2 on certain B cells. Extension of this work to the transplantation setting in a skin graft model in mice has illustrated effectiveness, where C3- and C4-deficient mice had a marked defect in allo-antibody production, due to failure of class switching to high-affinity IgG. The importance of these mechanisms in renal transplantation is increased due to the significance of anti-donor antibodies and humoral rejection.

In the setting of renal transplantation, tubular cells that produce complement also demonstrate complement deposition on their cell surface. These observations suggest the possibility that exposure of donor antigen to T-cells first occurs in the graft and that locally synthesized complement enhances antigen presentation, either by opsonization of donor antigen or by providing additional signals to both antigen-presenting cells and T-cells.

Tissue or solid organ transplantation mediated inflammatory reaction is also prevented by administering a composition comprising a therapeutically effective amount of Dextran Sulfate (alone or in combination with an antiplatelet agent) to the transplant recipient, including subjects that have received allotransplantation or xenotransplantation of whole organs (e.g., kidney, heart, liver, pancreas, lung, cornea, etc.) or grafts (e.g., valves, tendons, bone marrow, etc.). Administration may occur during the acute period following transplantation or as long-term post transplantation therapy. The Dextrans Sulfate may be administered to the subject by intra-arterial, intravenous, intramuscular, subcutaneous or other parenteral administration, or potentially by oral administration for non-peptidergic inhibitors. Additionally or in lieu of post transplant administration, the subject may be treated with the Dextrans Sulfate prior to transplantation and/or during the transplant procedure, and/or by pretreating the organ or tissue to be transplanted with the Dextrans Sulfate. Pretreatment of the organ or tissue may include applying a solution, gel or paste containing Dextran Sulfate to the surface of the organ or tissue by spraying or irrigating the surface. The organ or tissue may also be soaked in a Dextran Sulfate solution.

Central and Peripheral Nervous System Disorders and Injuries

Activation of the complement system has been implicated in the pathogenesis of a variety of central nervous system (CNS) or peripheral nervous system (PNS) diseases or injuries, including but not limited to multiple sclerosis (MS), myasthenia gravis (MG), Huntington's disease (HD), amyotrophic lateral sclerosis (ALS), Guillain Bane syndrome, reperfusion following stroke, degenerative discs, cerebral trauma, Parkinson's disease (PD) and Alzheimer's disease (AD). It has now been shown that C3a receptors and C5a receptors are found on neurons and show widespread distribution in distinct portions of the sensory, motor, and limbic brain systems. The role of complement in CNS disorders has been identified by the initial determination that complement proteins are synthesized in CNS cells including neurons, astrocytes and microglia, as well as the realization that anaphylatoxins generated in the CNS following complement activation can alter neuronal function. Moreover, the anaphylatoxins C5a and C3a have been shown to alter eating and drinking behavior in rodents and can induce calcium signaling in microglia and neurons. These findings raise possibilities regarding the therapeutic utility of inhibiting complement activation in a variety of CNS inflammatory diseases including cerebral trauma, demyelination, meningitis, stroke, and Alzheimer's disease.

A common clinical problem is the occurrence of brain trauma or hemorrhage and activation of complement system may occur and worsen resulting inflammation and edema, which has led to the study of complement inhibition in a model of brain trauma in rats. Administration of sCR1 immediately prior to brain injury markedly inhibited neutrophil infiltration into the injured area, indicating complement was important for recruitment of phagocytic cells. Likewise, complement activation in patients following cerebral hemorrhage is clearly implicated by the presence of high levels of multiple complement activation products in both plasma and cerebrospinal fluid (CSF). Complement activation and increased staining of C5b-9 complexes have been demonstrated in sequestered lumbar disc tissue. This could suggest a role in disc herniation tissue-induced sciatica.

MS is characterized by a progressive loss of myelin ensheathing and insulating axons within the CNS, and although the initial cause is unknown, there is abundant evidence implicating the immune system. There is also clear evidence that complement plays a prominent role in the pathophysiology of CNS or PNS demyelinating diseases including MS, Guillain-Barre syndrome and Miller-Fisher syndrome. Despite clear evidence of complement involvement, the identification of complement therapeutic targets is only now being evaluated in experimental allergic encephalomyelitis (EAE), an animal model of multiple sclerosis. Complement contributes to tissue destruction, inflammation, clearance of myelin debris and even remyelination of axons. Studies have established that EAE mice deficient in C3 or factor B showed attenuated demyelination as compared to EAE control mice. EAE mouse studies using a soluble form of a complement inhibitor coined "sCrry" and C3−/− and factor B−/− demonstrated that complement contributes to the development and progression of the disease model at several levels. In addition, the marked reduction in EAE severity in factor B−/− mice provides further evidence for the role of the alternative pathway of complement in EAE.

MG is a disease of the neuromuscular junction with a loss of acetylcholine receptors and destruction of the end plate. The histological hallmarks of AD, a neurodegenerative disease, are senile plaques and neurofibrillary tangles. sCR1 is very effective in an animal model of MG, further indicating the role of complement in the disease. These pathological markers also stain strongly for components of the complement system. Evidence points to a local neuroinflammatory state that results in neuronal death and cognitive dysfunction. Senile plaques contain abnormal amyloid-β-peptide (Aβ), a peptide derived from amyloid precursor protein. Aβ has been shown to bind C1 and can trigger complement activation. In addition, a prominent feature of AD is the association of activated proteins of the classical complement pathway from C1q to C5b-9, which have been found highly localized in the neuritic plaques. Thus, AP initiates the classical pathway, as well as neuronal cell death due to a resulting continual inflammatory state. Moreover, the fact that complement activation in AD has progressed to the terminal C5b-9 phase indicates that the regulatory mechanisms of the complement system have been unable to halt the complement activation process.

Several inhibitors of the complement pathway have been proposed as potential therapeutic approaches for AD, including proteoglycan as inhibitors of C1Q binding, Nafamstat as an inhibitor of C3 convertase, and C5 activation blockers or inhibitors of C5a receptors. Supported by the wealth of data suggesting complement pathway involvement in AD, the role of C3b as an initiation step in the innate complement pathway, as well as for alternative pathway activation, provides a potential new therapeutic approach. In damaged regions in the brains of PD patients, as in other CNS degenerative diseases, there is evidence of inflammation characterized by glial reaction (especially microglia), as well as increased expression of HLA-DR antigens, cytokines, and components of complement. This raises strong suggestions that immune system mechanisms are involved in the pathogenesis of neuronal damage in PD. The cellular mechanisms of primary injury in PD have not been clarified, however, but it is likely that mitochondrial mutations, oxidative stress, and apoptosis play a role. In addition, it is found that neuronal damage initiated inflammation in the striatum and the substantial nigra in PD, has the capacity to aggravate the course of the disease. These observations suggest that treatment with complement inhibitory drugs may act to slow progression of PD.

One aspect of the invention is thus directed to a method of treating of a subject suffering from peripheral nervous system (PNS) and/or central nervous system (CNS) disorders or injuries by administering a therapeutically effective amount of a Dextran Sulfate (alone or in combination with an antiplatelet agent) to the subject. CNS and PNS disorders and injuries that may be treated in accordance with the present invention are believed to include but are not limited to Miller-Fisher syndrome, multiple sclerosis (MS), Alzheimer's disease (AD), Parkinson's disease (PD myasthenia gravis (MG), Huntington's disease (HD), amyotrophic lateral sclerosis (ALS), Guillain Barre syndrome, reperfusion following stroke, degenerative discs, cerebral trauma,), cerebral trauma and/or hemorrhage, demyelination and, possibly, meningitis.

For treatment of CNS conditions and cerebral trauma, the Dextran Sulfate may be administered to the subject by intramuscular, intrathecal, intraventricular, intracranial, intra-arterial, subcutaneous, intravenous, or other parenteral administration, and potentially orally for non-peptidergic inhibitors. Treatment of PNS conditions and cerebral trauma may also include systemic administration or local administration to the site of dysfunction or trauma. Administration of the Dextran Sulfate compositions of the present invention may be repeated periodically as determined by a physician until effective relief or control of the symptoms is achieved.

Blood Disorders

Sepsis is a serious condition in which there is an overwhelming reaction of the immune response to invading microorganisms. A major function of the complement system is to orchestrate the inflammatory response to invading bacteria and other pathogens, therefore it is thought to have a major role in the pathogenesis of sepsis, as has been shown in numerous studies. The definition of the clinical manifestations of sepsis is ever evolving. Sepsis is usually defined as the systemic host response to an infection. However, on many occasions in patients with septic symptoms, no clinical evidence for infection is found. This discrepancy was first taken into account at a Consensus Conference in 1992 when the term "systemic inflammatory response syndrome" (SIRS) was established, and for which no definable presence of bacterial infection was required. It is now generally agreed upon that sepsis and SIRS are accompanied by the regulation incapacity of the inflammatory response. For the purposes of this brief review, we will consider the clinical definition of sepsis to include severe sepsis, septic shock, and SIRS. The predominant source of infection in septic patients before the late 1980s was Gram-negative bacteria. The main component of the Gram-negative bacterial cell wall, Lipopolysaccharide (LPS), was known to motivate release of inflammatory mediators from various cell types and provoke acute infectious symptoms when injected into animals.

Interestingly, the spectrum of responsible microorganisms appears to have shifted from predominantly Gram-negative bacteria in the late 1970s and 1980s to predominantly Gram-positive bacteria at present, for reasons that are currently unclear. Numerous studies have illustrated the importance of complement activation in mediating inflammation as well as the contribution to the features of shock, particularly septic and hemorrhagic shock. Both Gram-negative and Gram-positive organisms commonly precipitate septic shock. The major components of the Gram-positive cell wall are peptidoglycan and lipoteichoic acid, and both components are potent activators of the alternative complement pathway, although in the presence of specific antibodies they can also activate the classical complement pathway.

The complement system was initially implicated in the pathogenesis of sepsis when it was noted by researchers that anaphylatoxins C3a and C5a mediate a variety of inflammatory reactions that might also occur during sepsis. These anaphylatoxins evoke vasodilation and an increase in microvascular permeability, events that play a central role in septic shock. In addition, the anaphylatoxins induce bronchospasm, histamine release from mast cells, and aggregation of platelets. Moreover, they exert numerous effects on granulocytes, such as adhesion, chemotaxis, aggregation, release of lysosomal enzymes, generation of toxic super oxide anion, and formation of leukotrienes. These biologic effects are thought to play a role in development of complications of sepsis such as shock or acute respiratory distress syndrome (ARDS). Furthermore, elevated levels of the anaphylatoxin C3a is associated with a fatal outcome in sepsis. Certain complement-deficient strains (e.g., C5-deficient ones) are more resistant to the effects of LPS infusions, in some animal models of shock.

The prevention of C5a generation with antibodies during the arrival of sepsis in rodents has been shown to greatly improve survival, while related findings were made when the C5a receptor (C5aR) was blocked, using either antibodies or a small molecular inhibitor. Despite earlier experimental studies in monkeys that suggested antibody blockade of C5a attenuated E. coli induced septic shock and adult respiratory distress syndrome. In humans with sepsis, when compared with that in less severely septic patients and survivors, C5a was elevated and associated with significantly reduced survival rates together with multi-organ failure. The mechanisms by which C5a exerts its harmful effects during sepsis are yet to be investigated in detail, but recent data suggests that the generation of C5a during sepsis significantly compromises innate immune functions of blood neutrophils, their ability to express a respiratory burst, and their ability to generate cytokines. In addition, C5a generation during sepsis appears to have procoagulant effects. The complement-modulating protein CI INH has also shown efficacy in animal models of sepsis and ARDS.

The lectin pathway may also have a role in pathogenesis of sepsis. MBL has been shown to bind to a range of clinically important microorganisms including both Gram-negative and Gram-positive bacteria. MBL has also been shown to have the ability to activate the alternative pathway. Lipoteichoic acid (LTA) is increasingly regarded as the Gram-positive counterpart of LPS and is a potent immunostimulant that induces cytokine release from mononuclear phagocytes and whole blood.

An aspect of the invention thus provides a method for treating sepsis or a condition resulting from sepsis. It is possible to treat a suffering from sepsis or a condition resulting from sepsis including without limitation severe sepsis, septic shock, acute respiratory distress syndrome resulting from sepsis, and systemic inflammatory response syndrome by administering to the subject a composition comprising a therapeutically effective amount of Dextrans Sulfate (alone or in combination with a antiplatelet agent). Related methods are provided for the treatment of other blood disorders, including hemorrhagic shock, autoimmune thrombotic thrombocytopenic purpura (TTP), hemolytic anemia, hemolytic uremic syndrome (HUS) or other marrow/blood destructive conditions, by administering a composition comprising a therapeutically effective amount of Dextran Sulfate alone or in combination with an antiplatelet agent to a subject suffering from such a condition. The Dextran Sulfate can be administered to the subject systemically, such as by intra-arterial, intravenous, intramuscular, inhalational (particularly in the case of ARDS), subcutaneous or other parenteral administration, or potentially by oral administration for non-peptidergic agents. Combination is possible of the Dextran Sulfate composition with one or more additional therapeutic agents to combat the sequelae of sepsis and/or shock. For advanced sepsis or shock or a distress condition resulting from, the C3b inhibitory composition may suitably be administered in a fast-acting dosage form, such as by intravenous or intra-arterial delivery of a bolus of a solution containing the Dextrans Sulfate composition. Repetitive administration of the agent may be necessary until the condition has been resolved, as determined by a physician.

Urogenital Conditions

The complement system has been implicated in several distinct urogenital disorders including painful bladder disease, sensory bladder disease, chronic abacterial cystitis and interstitial cystitis, infertility, pregnancy, fetomaternal tolerance, and pre-eclampsia.

Sensory bladder disease, painful bladder disease, chronic abacterial cystitis and interstitial cystitis are ill-defined conditions of unknown etiology and pathogenesis, and, therefore, they are without any rational therapy. The dominating pathogenetic theories often concern defects in the epithelium and/or mucous surface coating of the bladder, as well as immunological disturbances. Patients with interstitial cystitis were reported to have been tested for immunoglobulin (IgA, G, M), complement components (C1q, C3, C4), and C1-esterase inhibitor. Resulting in findings that immunoglobulin G was markedly elevated (p less than 0.001) and a significant depletion of serum levels of complement component C4 (p less than 0.001). This study suggests classical pathway activation of the complement system, and supports the possibility that a chronic local immunological process is involved in the pathogenesis of the disease. Moreover, following binding of autoantibodies to antigens in bladder mucosa, activation of complement could be involved in the production of tissue injury and in the chronic self-perpetuating inflammation typical of this disease.

In addition to the role of complement in urogenital inflammatory diseases, reproductive functions may be impacted by the local regulation of the complement pathway. Naturally occurring complement inhibitors have evolved to provide host cells with the protection they need to control the body's complement system. A naturally occurring rodent complement inhibitor that is structurally similar to the human complement inhibitors, MCP and DAF, called Crry, has been investigated to delineate the regulatory control of complement in fetal development. Interestingly, attempts to generate Crry−/− mice were unsuccessful. Instead, it was discovered that homozygous Crry−/− mice died in utero. Crry−/− embryos survived until about 10 days post coitus, and survival rapidly declined with death resulting from developmental arrest. There was also a marked invasion of inflammatory cells into the placental tissue of Crry−/− embryos. In contrast, Crry+/+ embryos appeared to have C3 deposited on the placenta. This deposition suggests that complement activation occurred at the placenta level. In the absence of complement regulation, the embryos died. Confirming studies investigated the introduction of the Crry mutation onto a C3 deficient background, which was successful. Together, these data illustrate that the fetomaternal complement interface must be regulated. Subtle alterations in complement regulation within the placenta might contribute to placental dysfunction and miscarriage.

Pre-eclampsia is a pregnancy-induced hypertensive disorder in which complement system activation has been implicated but remains controversial. Even though no elevations were seen prior to the presence of clinical symptoms, complement activation in systemic circulation is closely related to established disease in pre-eclampsia, therefore, complement components cannot be used as predictors of pre-eclampsia. However, increased complement activation at the local environment of the placenta bed might overcome local control mechanisms, resulting in raised levels of anaphylatoxins and C5b-9.

One proposed mechanism of infertility related to anti-sperm antibodies (ASA) is through the role of complement activation in the genital tract. Elevated C5b-9 levels have been demonstrated in ovarian follicular fluid of infertile women. Generation of C3b and iC3b opsonin, which can potentiate the binding of sperm by phagocytic cells via their complement receptors as well as formation of the terminal C5b-9 complex on the sperm surface, thereby reducing sperm motility, are potential causes associated with reduced fertility. Other studies have shown impairment in sperm migration, and reduced sperm/egg interactions, which may be complement associated. Finally, studies with sCR1 demonstrated a protective effect against ASA- and complement mediated injury to human sperm. These data provide several lines of evidence for the use of complement inhibitors in the treatment of urogenital disease and disorders.

Another aspect of the invention thus relates to a method of inhibiting AP-dependent complement activation in a patient suffering from a urogenital disorder by administering a composition comprising a therapeutically effective amount of a Dextran Sulfate (alone or in combination with an antiplatelet agent). Some of the urogenital disorders thought to be subject to treatment with the methods and compositions related to the present invention include but are not limited to, sensory bladder disease, painful bladder disease, chronic abacterial cystitis and interstitial cystitis, male and female infertility, placental dysfunction and miscarriage and pre-eclampsia. The Dextran Sulfate composition may be delivered locally to the urogenital tract, such as by intravesical irrigation or instillation with a liquid solution or gel composition. Alternatively, the Dextran Sulfate may be administered to the subject systemically, such as by intra-arterial, intravenous, intramuscular, inhalational, subcutaneous or other parenteral administration, or potentially by oral administration for non-peptidergic agents. Repeated administration may be carried out as determined by a physician to control or resolve the condition.

Diabetes and Diabetic Conditions

Complement system activation can cause increased permeability, leukostasis, microthrombosis, and apoptosis of capillary cells, all of which are characteristic of diabetic retinal microangiopathy. Glomerular structures and endoneurial microvessels of patients with diabetes show signs of complement activation. Decreased availability or effectiveness of complement inhibitors in diabetes has been suggested by the findings that high glucose in vitro selectively decreases on the endothelial cell surface the expression of CD55 and CD59, the two inhibitors that are glycosylphosphatidylinositol (GPI)-anchored membrane proteins, and that CD59 undergoes nonenzymatic glycation that hinders its complement-inhibitory function.

Studies by Zhang et al., investigated complement activation and the association with changes in inhibitory molecules as well as a feature of human nonproliferative diabetic retinopathy. Deposition of C5b-9, the terminal product of complement activation, was found to occur in the wall of retinal vessels of human eye donors with type-2 diabetes, but not in the vessels of age-matched nondiabetic donors. C1q and C4, the complement components unique to the classical pathway were not found in the diabetic retinas, which indicate that C5b-9 was generated via the alternative pathway. In the diabetic donors the retinal levels of CD55 and CD59, the two complement inhibitors linked to the plasma membrane by GPI anchors were found to be dramatically reduced. Similar complement activation in retinal vessels and selective reduction in the levels of retinal CD55 and CD59 were observed in rats with a ten week duration of streptozotocin-induced diabetes. Thus, diabetes appears to cause defective regulation of complement inhibitors and complement activation that precede most other manifestations of diabetic retinal microangiopathy. Gerl et al. determined the presence of activated complement components in eyes affected by diabetic retinopathy.

Extensive deposits of complement C5b-9 complexes were detected in the choriocapillaris immediately underlying the Bruch membrane and densely surrounding the capillaries in all 50 diabetic retinopathy specimens following immunohistochemical study. Staining for C3d positively correlated with C5b-9 staining, indicative of the fact that complement activation had occurred in situ. Furthermore, positive staining was found for vitronectin, which forms stable complexes with extracellular C5b-9. In contrast, there was no positive staining for C-reactive protein (CRP), mannan-binding lectin (MBL), C1q, or C4, indicating that complement activation did not occur through a C4-dependent pathway. Thus, there are indications that the presence of C3d, C5b-9, and vitronectin illustrate complement activation completion occurs through the alternative pathway in the choriocapillaris of eyes affected by diabetic retinopathy. Complement activation may be a causative factor in the pathologic sequelae that can contribute to ocular tissue disease and visual impairment. Therefore, the use of a complement inhibitor may be an effective therapy to reduce or block damage to microvessels that occurs in diabetes.

Insulin dependent diabetes mellitus (IDDM, also referred to as Type-I diabetes) is an autoimmune disease associated with the presence of different types of autoantibodies. The presence of these antibodies and the corresponding antigens, which are known to persist in the blood for long periods, leads to the formation of circulating immune complexes (CIC). Deposition of CIC in the small blood vessels has the potential to lead to microangiopathy with debilitating clinical consequences. A correlation exists between CIC and the development of microvascular complications in diabetic children and findings suggest that elevated levels of CIC IgG are associated with the development of early diabetic nephropathy and that an inhibitor of the complement pathway may be effective at blocking diabetic nephropathy. In addition, the formation of downstream complement proteins and the involvement of the alternative pathway are likely to be a contributory factor in overall islet cell function in IDDM and the use of a complement inhibitor to reduce potential damage or limit cell death is expected.

Another aspect of the invention thus relates to a method of inhibiting AP-dependent complement activation in a subject suffering from non-obese diabetes (IDDM) or from angiopathy, neuropathy or retinopathy complications of IDDM or adult onset (Type-2) diabetes, by administering a composition comprising a therapeutically effective amount of a Dextran Sulfate (alone or in combination with an antiplatelet agent). There is also the option of administering the Dextran Sulfate to the subject systemically, such as by intra-arterial, intravenous, intramuscular, subcutaneous or other parenteral administration, or potentially by oral administration for non-peptidergic agents. Alternatively, administration may be by local delivery to the site of angiopathic, neuropathic or retinopathic symptoms. The Dextran Sulfate can also be administered periodically over an extended period for treatment or control of a chronic condition, or by a single or series of administrations for treatment of an acute condition.

Perichemotherapeutic Administration and Treatment of Malignancies

Activation of the complement system may also be implicated in the pathogenesis of malignancies. Recently, the neoantigens of the C5b-9 complement complex, IgG, C3, C4, S-protein/vitronectin, fibronectin, and macrophages were localized on breast cancer using polyclonal or monoclonal antibodies and the streptavidin-biotin-peroxidase technique. All the tissue samples with carcinoma in each the TNM stages presented C5b-9 deposits on the membranes of tumor cells, thin granules on cell remnants, and diffuse deposits in the necrotic areas. In addition, complement activation may be a consequence of chemotherapy or radiation therapy and thus inhibition of complement activation would be useful as an adjunct in the treatment of malignancies to reduce iatrogenic inflammation. C5b-9 deposits were more intense and extended when chemotherapy and radiation therapy preceded surgery. The C5b-9 deposits were absent in all the samples with benign lesions. S-protein/vitronectin was present as fibrillar deposits in the connective tissue matrix and as diffuse deposits around the tumor cells, less intense and extended than fibronectin. IgG, C3, and C4 deposits were present only in carcinoma samples. The presence of C5b-9 deposits is indicative of complement activation and its subsequent pathogenetic effects in breast cancer. Pulsed tunable dye laser (577 nm) (PTDL) therapy induces hemoglobin coagulation and tissue necrosis, which is mainly limited to blood vessels. In a PTDL-irradiated normal skin study, the main findings were as follows: 1) C3 fragments, C8, C9, and MAC were deposited in vessel walls, 2) Deposits were not due to denaturation of the proteins since they became apparent only 7 min after irradiation, contrary to immediate deposition of transferrin at the sites of erythrocyte coagulates, 3) C3 deposits were shown to amplify complement activation by the alternative pathway, a reaction which was specific since tissue necrosis itself did not lead to such amplification, 4) These reactions preceded the local accumulation of polymorphonuclear leucocytes.

Tissue necrosis was more pronounced in the hemangiomas. The larger angiomatous vessels in the center of the necrosis did not fix complement significantly. By contrast, complement deposition in the vessels situated at the periphery was similar to that observed in normal skin with one exception: C8, C9, and MAC were detected in some blood vessels immediately after laser treatment, a finding consistent with assembly of the MAC occurring directly without the formation of a C5 convertase. These results indicate that complement is activated in PTDL-induced vascular necrosis, and might be responsible for the ensuing inflammatory response.

Photodynamic therapy (PDT) of tumors elicits a strong host immune response, and one of its manifestations is a pronounced neutrophilia. In addition to complement fragments (direct mediators) released because of PDT-induced complement activation, there are at least a dozen secondary mediators that all arise because of complement activity. The latter include cytokines IL-1β, TNF-α, IL-6, IL-10, G-CSF and KC, thromboxane, prostaglandins, leukotrienes, histamine, and coagulation factors.

Finally, in conjunction with the standard therapeutic regimen for the treatment of cancer, the use of inhibitors of C3b-dependent complement activation may be added. For example, treatment with rituximab, a chimeric anti-CD20 monoclonal antibody is known to cause moderate to severe first-dose side effects, mostly in patients with high numbers of circulating tumor cells. Recent studies during the first infusion of rituximab measured complement activation products (C3b/c and C4b/c) and cytokines (tumour necrosis factor alpha (TNF-alpha), interleukin 6 (IL-6) and IL-8) in five relapsed low-grade non-Hodgkin's lymphoma (NHL) patients. Infusion of rituximab induced rapid complement activation, preceding the release of TNF-alpha, IL-6 and IL-8. Although the study group was small, the level of complement activation appeared to be correlated both with the number of circulating B cells prior to the infusion (r=0.85; P=0.07), and with the severity of the side effects. The results indicated that complement plays a pivotal role in the pathogenesis of side effects of rituximab treatment. As complement activation cannot be prevented by corticosteroids, it may be relevant to study the possible role of complement inhibitors during the first administration of rituximab.

In another aspect of the invention, methods are provided for inhibiting AP-dependent complement activation in a subject being treated with chemotherapeutics and/or radiation therapy, including without limitation for the treatment of cancerous conditions. This method includes administering a composition comprising a therapeutically effective amount of a Dextran Sulfate (alone or in combination with an antiplatelet agent) to a patient perichemotherapeutically, i.e., before and/or during and/or after the administration of chemotherapeutic(s) and/or radiation therapy. For example, administration of a Dextran Sulfate composition may be commenced before or concurrently with chemo- or radiation therapy, and continued throughout the course or following the therapy. This could be used to reduce the detrimental effects of the chemo- and/or radiation therapy in the non-targeted, healthy tissues. It is understood that chemo- and radiation therapy regimens often entail repeated treatments and, therefore, it is possible that administration of a Dextran Sulfate composition would also be repetitive and relatively coincident with the chemotherapeutic and radiation treatments. It is also believed that Dextran Sulfate may be used as chemotherapeutic agents, alone or in combination with other chemotherapeutic agents and/or radiation therapy, to treat patients suffering from malignancies. Examples of administration may be via oral (for non-peptidergic), intravenous, intramuscular, or other parenteral route.

Endocrine Disorders

The complement system has also been recently associated with a few endocrine conditions or disorders including Hashimoto's thyroiditis, stress, anxiety and other potential hormonal disorders involving regulated release of prolactin, growth or insulin-like growth factor, and adrenocorticotropin from the pituitary Ophthalmologic Conditions Age-related macular degeneration (AMD) is a blinding disease that afflicts millions of adults, and results in the progressive destruction of the macula that has been correlated with the formation of extracellular deposits called drusen located in and around the macula, behind the retina and between the retina pigment epithelium (RPE) and the choroid. Recent studies have revealed that prevalent among drusen-associated individuals are proteins associated with inflammation and immune-mediated processes. Transcripts that encode a number of these molecules have been detected in retinal, RPE, and choroidal cells. This data also demonstrates that dendritic cells, which are potent antigen-presenting cells, are intimately associated with drusen development, and that complement activation is a key pathway that is active both within drusen and along the RPE-choroid interface.

Strong association between AMD and a genetic polymorphism, has been found by numerous independent studies, in the gene for complement factor H (CFH) in which the likelihood of AMD is increased by a factor of 7.4 in individuals homozygous for the risk allele. The CFH gene has been mapped to chromosome 1q31 a region that had been implicated in AMD by six independent linkage scans (see, e.g., D. W. Schultz et al). CFH is known to be a key regulator of the complement system. It has been shown that CFH on cells and in circulation regulates complement activity by inhibiting the activation of C3 to C3a and C3b, and by inactivating existing C3b. Deposition of C5b-9 has been observed in Brusch's membrane, the intercapillary pillars and within drusen in patients with AMD. Immunofluorescence experiments suggest that in AMD, the polymorphism of CFH may give rise to complement deposition in chorodial capillaries and chorodial vessels.

The membrane-associated complement inhibitor, complement receptor 1, is also localized in drusen, but it is not detected in RPE cells immunohistochemically. In contrast, a second membrane-associated complement inhibitor, membrane cofactor protein, is present in drusen-associated RPE cells, as well as in small, spherical substructural elements within drusen. These previously unidentified elements also show strong immunoreactivity for proteolytic fragments of complement component C3 that are characteristically deposited at sites of complement activation. It is proposed that these structures represent residual debris from degenerating RPE cells that are the targets of complement attack.

An aspect of the invention thus provides a method for inhibiting AP-dependent complement activation to treat age-related macular degeneration or other complement mediated ophthalmologic condition by administering a composition comprising a therapeutically effective amount of a Dextrans Sulfate (alone or in combination with an antiplatelet agent) to a subject suffering from such a condition or other complement-mediated ophthalmologic condition. The complement inhibitory composition may be administered locally to the eye, such as by irrigation or application of the composition in the form of a gel, salve or drops. Alternately, the Dextran Sulfate may be administered to the subject systemically, such as by intra-arterial, intravenous, intramuscular, inhalational, nasal, subcutaneous or other parenteral administration, or potentially by oral administration for non-peptidergic agents. The Dextrans Sulfate composition may be combined with one or more additional therapeutic agents. Administration may be repeated as determined by a physician until the condition has been resolved or is controlled.

Brain Injury

Complement activation has been shown to play an important role in this clinical condition traumatic brain injury (Bellander et al., 2001, J. Neurotrauma 18:1295-1311; Kaczorowski et al., 1995, J. Cereb. Blood Flow Metab. 15:860-864; Keeling et al., 2000, J. Neuroimmunol. 105:20-30; Schmidt et al., 2004, Eur. J. Trauma 30:135-149; Nataf et al., 1999, Trends Neurosci 22:397-402; Stahel et al., 1998, Brain Res. Rev. 27:243-256; Stahel et al., 2001, J. Neurotrauma 18:773-781; Van Beek et al., 2003, Ann NY Acad Sci 992:56-71; Rancan et al., 2003, J. Cereb. Blood Flow & Metab. 23:1070-1074).

The immediate goal in the treatment of head-injured patients is the prevention of cellular and complement activation. Spinal Cord Injury: SCI is also a condition of the central nervous system. Complement plays an important role in further damage following brain injury. (Anderson et al., 2004, J Neurotrauma 21(12):1831-46; Reynolds et al., 2004, Ann NY Acad Sci. 1035:165-78; Rebhun et al., 1991, Ann Allergy 66(4):335-8). SCI is generally defined as damage to the spinal cord that results in a loss of function, such as mobility or feeling. Frequent causes of damage are trauma (e.g., by car accident, gunshot, falls, etc.) or disease (polio, spina bifida, Friedreich's Ataxia, etc.).

An aspect of the invention thus provides a method for inhibiting AP-dependent complement activation to brain injury, central nervous system injury, or peripheral nervous system injury by administering a composition comprising a therapeutically effective amount of a Dextrans Sulfate (alone or in combination with an antiplatelet agent) to a subject suffering from such a condition.

It is to be noted that throughout this application various publications and patents are cited. The disclosures of these publications are hereby incorporated by reference in their entireties into this application in order to describe fully the state of the art to which this invention pertains.

The Examples that follow illustrate embodiments of the present invention and are not limiting of the specification and claims in any way. In the following Examples, Dextran Sulfate with a molecular weight of 40,000 Daltons has been named as NM3014 or NMDS. This molecule has an 18-20% by weight sulfate content.

EXAMPLE 1

Properdin Binds NM3014 (NMDS/Dextran Sulfate) with High Affinity

Polystyrene microtiter plates were coated with Dextran Sulfate polymer (0.5 .mu.g/50 .mu.l per well) (Pharmachem Corp) in PBS (Phosphate Buffered Saline) overnight at 4° C. After aspirating the Dextran Sulfate solution, wells were blocked with 1% BSA in PBS (Sigma Chemical Company, St. Louis, Mo., Cat. No. A7888) for 2 hours at room temperature. Wells without Dextran Sulfate coating served as background controls. Aliquots of human properdin (or factor P) (Advanced Research Technology, San Diego, Calif., Cat. No. A139) at varying concentrations in blocking solution were added to the wells. Following a 2 hour incubation at room temperature, the wells were extensively rinsed with PBS.

Dextran Sulfate-bound properdin was detected by the addition of mouse monoclonal anti-human properdin antibody (detection antibody) (Quidel, San Diego, Calif., anti-human properdin monoclonal antibody P#2, Cat. No. A235) at 1:1000 dilution in blocking solution, which was allowed to incubate for 1 hour at room temperature. After washing the plates with PBS, a peroxidase-conjugated goat anti-mouse antibody (1:1000 dilution in blocking solution) (Sigma Chemical Company) was added and allowed to incubate for 1 hour. The plate was again rinsed thoroughly with PBS, and 100 .mu.l of 3,3',5,5'-tetramethyl benzidine (TMB) substrate (Kirkegaard & Perry Laboratories, Gaithersburg, Md., Cat. No. A50-65-00) was added. After incubation for 10 minutes at 25° C., the reaction of TMB was quenched by the addition of 100 .mu.l of phosphoric acid, and the plate was read at 450 nm in a microplate reader (e.g., SPECTRA MAX 250, Molecular Devices, Sunnyvale, Calif.). The estimated affinity of 4 nM of properdin binding to Dextran Sulfate was based on the concentration of properdin at 50% maximal binding (Microcal Origin Program).

EXAMPLE 2

NM3014 in Solution Inhibits Properdin Binding to Substrate-Bound NM3014

Figure 4:
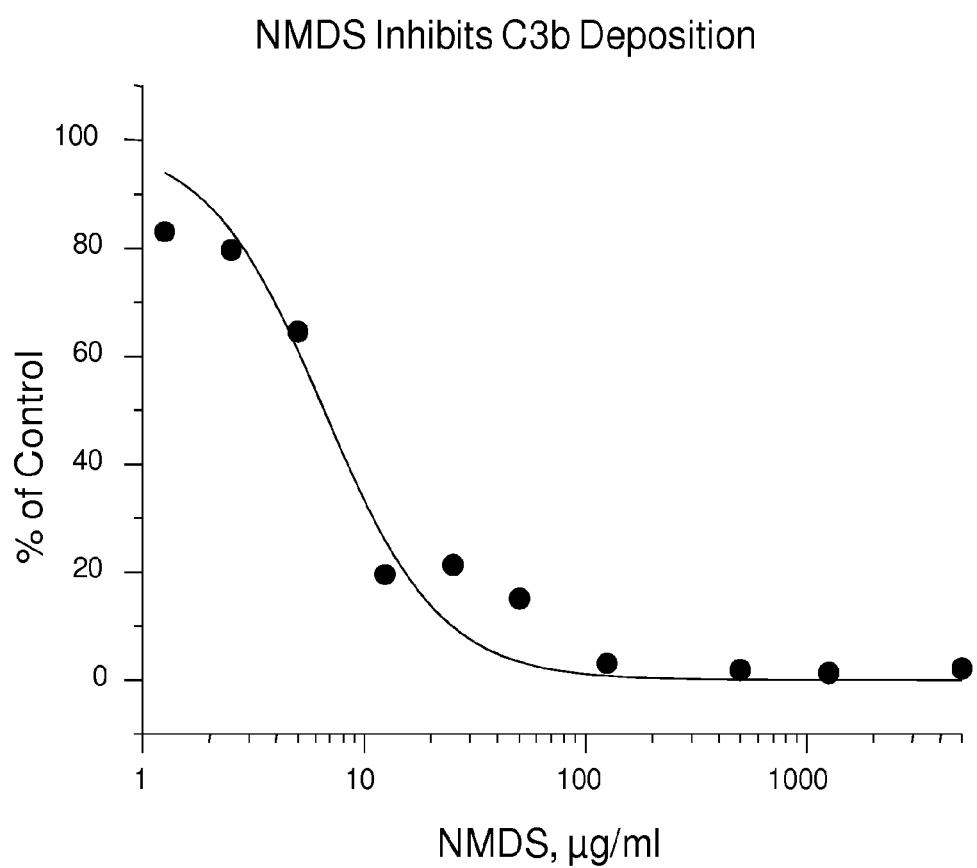
FIG. 4 illustrates NM3014 Inhibits Alternative Pathway Dependent C3b formation in Normal Human Serum: Normal Human Serum containing increasing concentrations of Dextran Sulfate (NM3014) was incubated on to LPS coated plates. LPS activated complement in human serum. As a result, C3b is generated and is deposited on to LPS. NM3014 inhibited C3b formation in a dose dependent manner. LPS bound C3b was detected with a rabbit anti-human C3c antibody (Dako Corp). Rabbit antibody bolund to C3b was detected with peroxidase-conjugated goat anti-rabbit polyclonal antibody. Peroxidase was detected with TMB substrate using common methods. The IC50 of the inhibition falls in the range of 7-10 µg/ml in 10% normal human serum.
Figure 5:
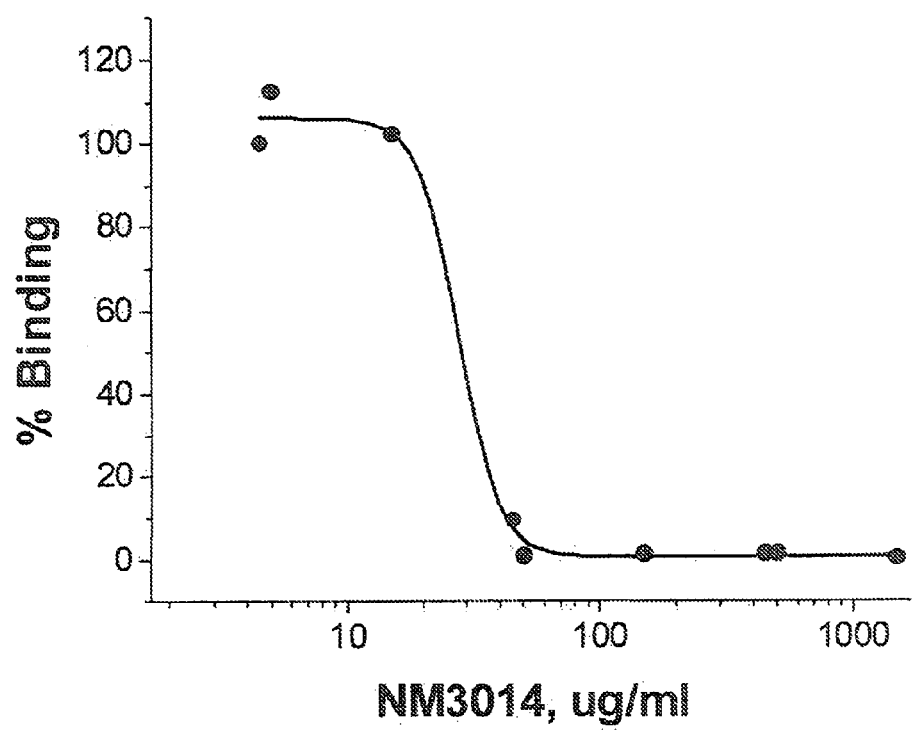
FIG. 5 illustrates NM3014 Inhibits C5b-9 Formation in Normal Human Serum: Polystyrene microtiter wells were coated with LPS. Wells were blocked with BSA. Uncoated wells served as background controls. ELISA wells were incubated with 8% NHS in AP buffer (GVB with MgCl2/EGTA) containing various concentrations of the Dextran Sulfate. The plate was then incubated at 37° for 45 min to allow complement activation to occur. Following this incubation, the deposited C5b-9 was detected with an anti-C5b-9 antibody (Quidel Corp). Following a one hour incubation, the ELISA plate was washed in PBS and the wells incubated with peroxidase-conjugated goat anti-mouse antibody. The plate was rinsed with PBS and the color was developed with TMB. The data was fitted using Microcal origin program to determine the IC50. The data is presented as the mean % binding of triplicate samples from a representative experiment. The experiment was replicated three times with similar results.

As shown in FIG. 4, human properdin binds to substrate-bound Dextran Sulfate, which has been immobilized onto microtiter plate wells. The apparent binding constant from these data, defined as the concentration of properdin needed to reach half-maximal binding, is approximately 4 nM. When Dextran Sulfate is added along with properdin in this assay, dose-dependent inhibition of properdin binding to Dextran Sulfate is observed (FIG. 5). As shown we tested the activity of chondroitin sulfate A, chondroitin sulfate C, and hyaluronic acid.

EXAMPLE 3

NM3014 Inhibits Properdin Binding to C3b with High Affinity

In a typical assay, polystyrene microtiter plates were coated with C3b (50 µg/50 µl/well, Advanced Research Technologies, San Diego, Calif.) in phosphate buffered saline (PBS) overnight at 4° C. After aspirating the C3b solution, wells were blocked with PBS containing 1% bovine serum albumin (BSA) (Sigma Chemical Company, St. Louis, Mo., Cat. No. A7888) for 2 hours at room temperature. Wells without C3b coating served as background controls. Aliquots of human properdin (or factor P) (Advanced Research Technology, San Diego, Calif., Cat. No. A139) at varying concentrations in blocking solution were added to the wells. Following a 2 hour incubation at room temperature, the wells were extensively rinsed with PBS. C3b-bound properdin was detected by the addition of mouse monoclonal anti-human properdin antibody (detection antibody) (Quidel, San Diego, Calif., anti-human properdin monoclonal antibody P#2, Cat. No. A235) at 1:2000 dilution in blocking solution, which was allowed to incubate for 1 hour at room temperature. After washing the plates with PBS, a peroxidase-conjugated goat anti-mouse antibody (1:1000 dilution in blocking solution) (Sigma Chemical Company) was added and allowed to incubate for 1 hour. The plate was again rinsed thoroughly with VBS, and 100 µl of 3,3',5,5'-tetramethyl benzidine (TMB) substrate (Kirkegaard & Perry Laboratories, Gaithersburg, Md., Cat. No. A50-65-00) was added. After incubation for 10 minutes at 25° C., the reaction of TMB was quenched by the addition of 100 µl of phosphoric acid, and the plate was read at 450 nm in a microplate reader (e.g., SPECTRA MAX 190, Molecular Devices, Sunnyvale, Calif.). The estimated Kd of properdin binding to C3b was based on the concentration of properdin at 50% maximal binding (Microcal Origin Program).

The ability of a Dextran Sulfate to inhibit C3b-P binding was evaluated by adding varying concentrations of Dextran Sulfate to a constant concentration of properdin (2 nM). The amount of properdin bound to C3b was detected with the antibody detection system described above.

Figure 6:
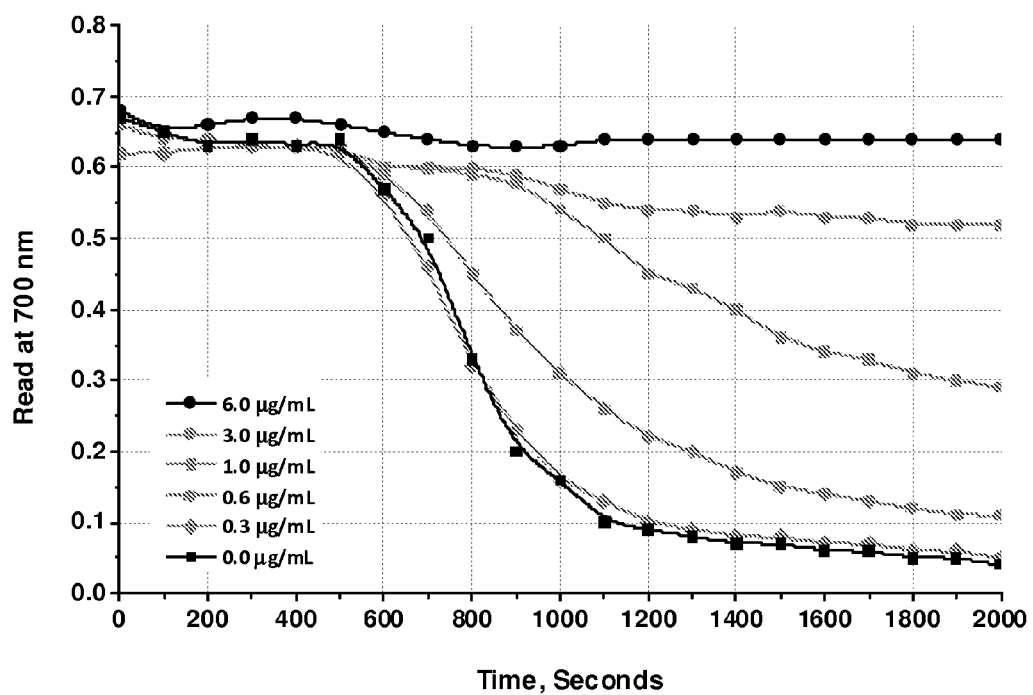
FIG. 6 illustrates NM3014 Inhibits Alternative Pathway (AP) Activation in a Rabbit Erythrocyte Assay: The first line starting from the bottom is a an untreated, the second line contains 1 µg/ml of Dextran Sulfate, the third line contains 3 µg/ml of Dextran Sulfate, the fourth line contains 10 µg/ml Dextran Sulfate, the fifth line contains 30 µg/ml of Dextran Sulfate, and the sixth line contains 60 µg/ml of Dextran Sulfate. X axis is time of hemolysis in seconds and Y-axis is scattering at 700 nm. Methods: Normal human serum 10% was incubated with rabbit erythrocytes in AP buffer with and without Dextran Sulfate. Various concentrations of Dextran Sulfate were used ranging from 1 to 60 µg/ml. Dextran Sulfate (NM3014) inhibits hemolysis as shown by decreased scattering at a concentration of 10 µg/ml. Total inhibition of complement AP was seen at 30 µg/ml concentration. Consistent results were obtained with multiple donors.

As shown in FIG. 6, human properdin binds to C3b, which has been immobilized onto microtiter plate wells. The apparent binding constant from these data, defined as the concentration of properdin needed to reach half-maximal binding, is approximately 1 nM. When Dextran Sulfate is added along with properdin in this assay, dose-dependent inhibition of properdin binding to C3b is observed (FIG. 6).

EXAMPLE 4

Alternative Pathway-Dependent C3b Assay

The hemolysis data above reveals that the Dextran Sulfate is a potent inhibitor of the alternative pathway dependent lysis of rabbit erythrocytes in normal human serum. It was of interest to us to determine whether the Dextran Sulfate might appreciably affect the C3b generation, an important component of the amplification loop of the complement cascade. To analyze the effects of the Dextran Sulfate on C3b formation via the alternative pathway, an assay was utilized in which bacterial LPS was used as a substrate to initiate the alternative complement pathway cascade. Previous studies have demonstrated that lipopolysaccharide (LPS) from *Salmonella typhosa* (*S. Typhosa*) (Sigma Chemical Company, Cat. No. 6386) serves as a potent substrate for complement alternative pathway activation (Clardy, C. W., 1994, Infect. Immun. 62:4539-4555). Microtiter wells were coated with LPS (2 µg/50 µl per well) in VBS overnight at 4° C. Uncoated wells served as background controls. After aspirating the LPS solution, wells were treated with blocking solution and incubated with various concentrations of normal human serum. Following a 2 hour incubation at 37° C., deposited C3b was detected with rabbit anti-human C3c polyclonal antibody (Accurate Biochemicals) using standard ELISA methodologies essentially as described in the Examples above. The effect of Dextran Sulfate on the C3B formation was evaluated by adding various concentrations of Dextran Sulfate blocking antibody to a fixed concentration of serum (4% in blocking solution). The amount of inhibition of soluble C3b deposition was determined using the antibody detection system described in the Examples above.

Figure 3:
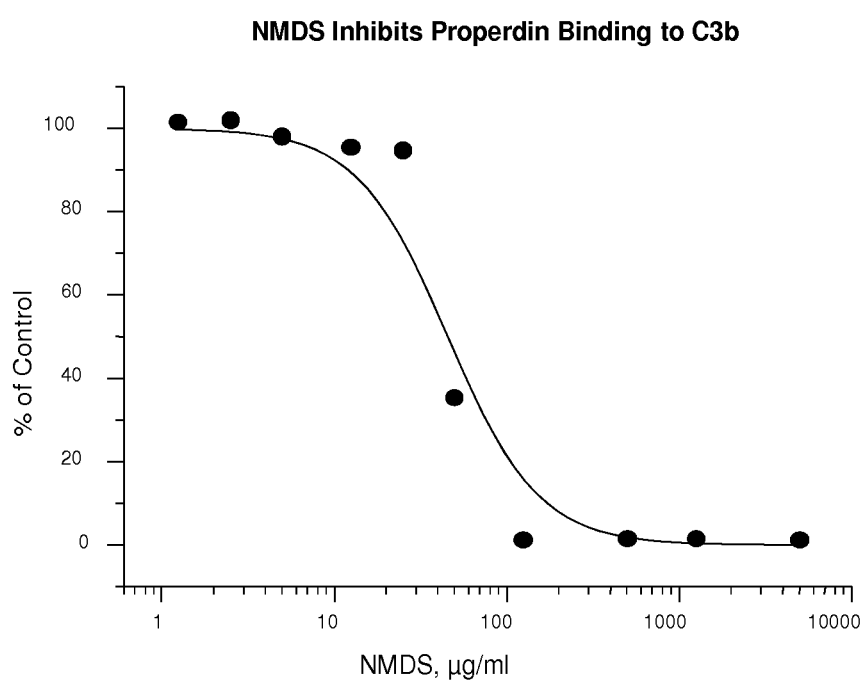
FIG. 3 illustrates NM3014 Inhibits Properdin Binding to C3b: Dextran Sulfate (NM3014 or NMDS) causes a dose-dependent and complete inhibition of properdin binding to C3b: The IC50 is in the range of 50 µg/ml. Methods: Polystyrene microtiter plates were coated with C3b in phosphate buffered saline (PBS) overnight. After aspirating the C3b solution, wells were blocked bovine serum albumin Wells without C3b coating served as background controls. Aliquots of human serum containing nearly 2-5 nM properdin with and without NMDS (NM3014), in blocking solution, were added to the wells and incubated for 2 hours at room temperature to allow properdin binding to occur. Wells were washed PBS and C3b-bound properdin was detected by the addition of a mouse anti-human properdin antibody (Quidel, P#2 monoclonal). After washing the plate with PBS, HRP-conjugated goat anti-mouse antibody (Sigma Chemicals A2304) was added and allowed to incubate for 1 h. The plate was again rinsed thoroughly with PBS, and TMB substrate was added to each well. The data was plotted using Microcal Origin Program.

As demonstrated in FIG. 3, addition of increasing amounts of Dextran Sulfate completely prevents C3b generation in a dose dependent manner These data indicate that Dextran Sulfate is a potent inhibitor of the alternative pathway.

EXAMPLE 5

Alternative Pathway-Dependent C5b-9 Assay; Dextrans Sulfate Inhibits C5b-9 in a Solid Phase Assay Dextran Sulfate is a potent inhibitor of the alternative pathway dependent lysis of rabbit erythrocytes in normal human serum. We wanted to determine whether the Dextran Sulfate will affect the terminal aspects of the alternative complement cascade. The final product of this pathway is the C5b-9 membrane-attack complex (MAC). A solid phase ELISA was utilized in which in which bacterial LPS was used as a substrate to start the alternative complement pathway cascade.

Previous studies have demonstrated that lipopolysacharide (LPS) from *Salmonella typhosa* (*S. Typhosa*) (Sigma Chemical Company, Cat. No. 6386) serves as a potent substrate for complement alternative pathway activation (Clardy, C. W., 1994, Infect. Immun. 62:4539-4555). Microtiter wells were coated with LPS (2 µg/50 µl per well) in VBS overnight at 4° C. Uncoated wells served as background controls. After aspirating the LPS solution, wells were treated with blocking solution and incubated with various concentrations of normal human serum. Following a 3 hour incubation at 37° C., deposited MAC was detected with mouse anti-human soluble C5b-9 monoclonal antibody (Quidel, Cat. No. A239) using standard ELISA methodologies essentially as described in the Examples above. The effect of the blocking antibody on the MAC formation was evaluated by adding various concentrations of blocking antibody to a fixed concentration of serum (8% in blocking solution). The amount of inhibition of soluble C5b-9 formation was determined using the antibody detection system described in the Examples above.

Figure 2:
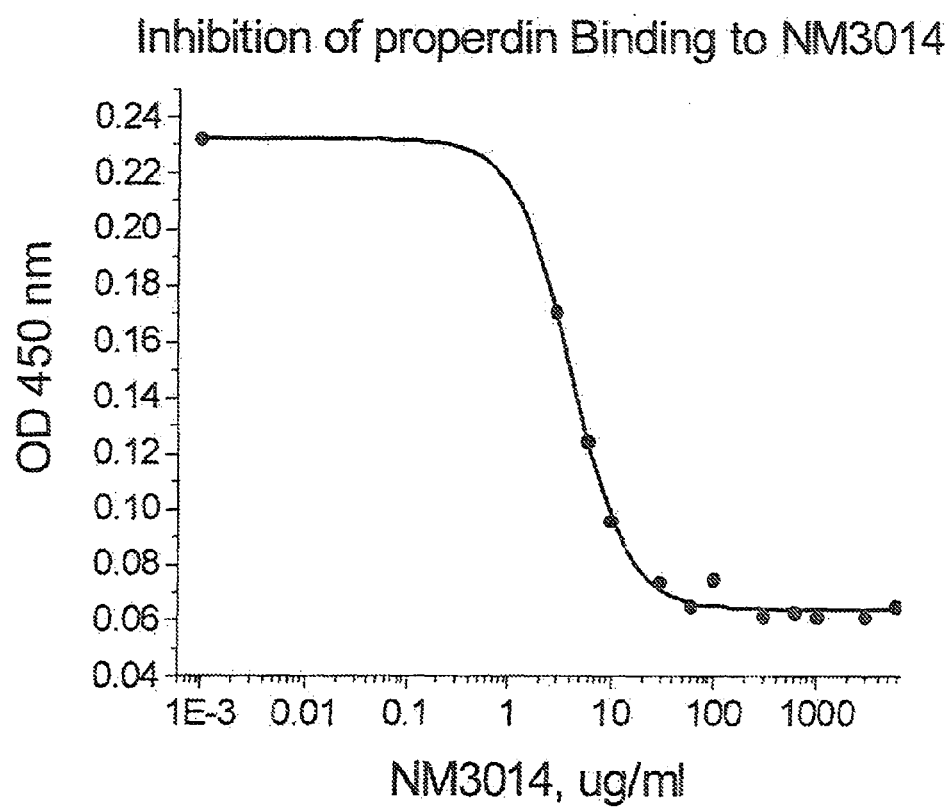
FIG. 2 illustrates NM3014 Inhibits Properdin Binding to Substrate-Bound Dextran Sulfate with high affinity and the present figure shows that such binding is inhibited by solution phase Dextran Sulfate (NM3014). Methods: Polystyrene microtiter plates were coated with Dextran Sulfate overnight. Wells without Dextran Sulfate coating served as background controls. After removal of the Dextran Sulfate solution, the plates were washed and blocked with 1% BSA in PBS. Properdin solution with and without Dextran Sulfate was added to the appropriate wells. After this incubation, properdin solution was aspirated from the plate and the plate was washed. The wells were then incubated with anti-properdin monoclonal antibody at a 1:2000 dilution in blocking solution to allow detection of Dextran Sulfate-bound properdin. The wells were rinsed and further incubated with peroxidase-conjugated goat anti-mouse IgG followed by another wash step. Dextran Sulfate-bound properdin was detected by the addition of TMB substrate. The reaction of TMB was quenched by the addition of O-phosphoric acid and the plate read at 450 nm. The data was fitted using Microcal origin program to determine the IC50.

As demonstrated in FIG. 2, the formation of MAC in this assay could be completely prevented by the addition of the Dextran Sulfate. These data indicate that Dextran Sulfate is a potent inhibitor of the alternative pathway.

EXAMPLE 6

Alternative Pathway-Dependent Hemolysis; Dextran Sulfate Inhibits C5b-9 Formation in Cellular Assay The Dextran Sulfate (40,000 molecular weight) was examined in the alternative pathway dependent hemolysis assay. Rabbit erythrocytes initiate the alternative complement cascade, and the resulting formation of MAC causes lysis of these cells. If the Dextran Sulfate is capable of complete inhibition of the alternative pathway, then addition of the reagent to rabbit erythrocytes bathed in human serum should prevent cellular lysis. This can be assayed by examining the light scattering caused by intact red blood cells; lysed cells do not diffract light, and there is a consequent reduction in scattered light. It is well established that rabbit erythrocytes specifically activate the complement alternative pathway, with a resulting lysis of the cells by the C5b-9 complex. Normal human serum, at various concentrations in Gelatin Veronal Buffer (GVB) (Advanced Research Technology) with 5 mM $MgCl_2$ and 10 mM EGTA, was incubated with 37° C.

with a fixed number of rabbit erythrocytes (Advanced Research Technology). A progressive decrease in light scatter (due to lysis of intact cells) was measured at 700 nm as a function of time in a temperature-controlled ELISA plate reader. To determine the ability of blocking antibody to inhibit hemolysis of rabbit erythrocytes, various concentrations of the blocking antibody were added to a fixed concentration of normal human serum (8%) and the assay was performed as described above. The data were recorded and analyzed with a SpectraMax 190 plate reader and SoftMax Pro software.

Figure 1:
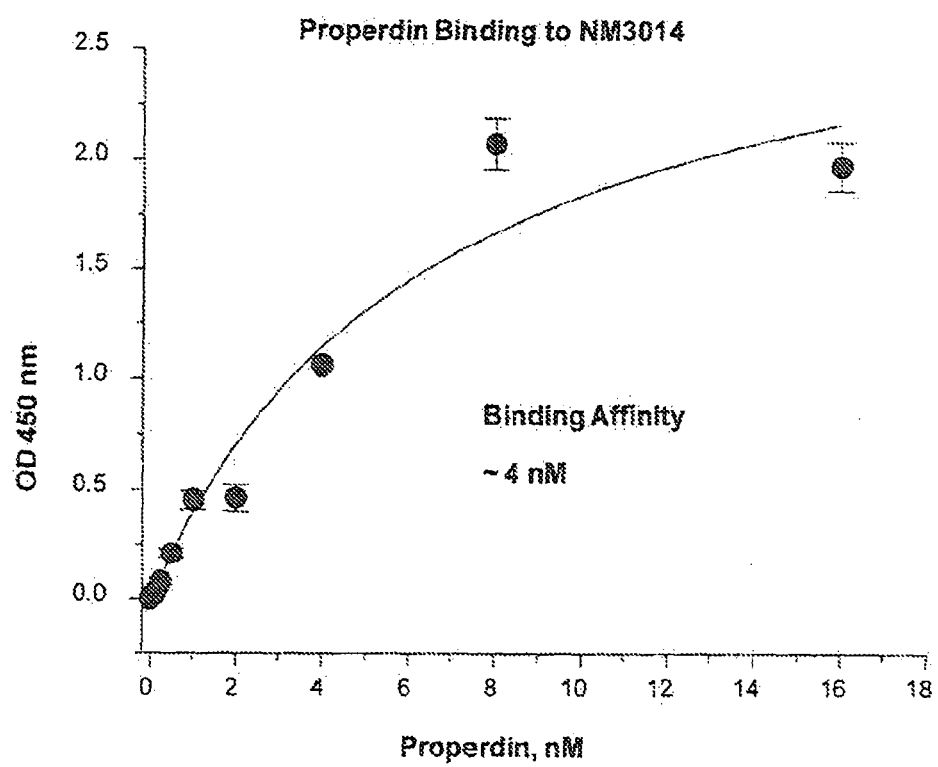
FIG. 1 illustrates Properdin Binds Dextran Sulfate (NM3014): Properdin was observed to bind with high affinity and specificity to Dextran Sulfate. The binding of properdin appears to be specific and dose dependent. Leading to an affinity of 4 nM. Methods: Polystyrene microtiter plates were coated with Dextran Sulfate overnight. Wells without Dextran Sulfate coating serve as background controls. After removal of the Dextran Sulfate solution, the plates were washed and blocked with 1% BSA in PBS. Properdin solution was added to the appropriate wells. After this incubation, properdin solution was aspirated from the plate and the plate was washed. The wells were then incubated with anti-properdin MoAb (Quidel, P#2) at a 1:2000 dilution in blocking solution to allow detection of Dextran Sulfate-bound properdin. The wells were rinsed and further incubated with peroxidase-conjugated goat anti-mouse IgG (Sigma A2304) followed by another wash step. Dextran Sulfate-bound properdin was detected by the addition of TMB substrate. The reaction of TMB was quenched by the addition of O-phosphoric acid and the plate read at 450 nm. results.

As shown in FIG. 1, addition of serum in the absence of Dextran Sulfate resulted in lysis of the cells and a dramatic reduction in light scattering. Addition of increasing concentrations of the Dextran Sulfate caused a decrement in erythrocyte lyses, with Dextran Sulfate completely blocking MAC-mediated cellular destruction. These results confirm that a carbohydrate polymer that blocks alternative pathway activation can be proposed as a therapeutic to treat conditions where AP plays a significant role.

Skilled artisans recognize and accept that in vitro studies of complement are representative of and predictive of the in vivo state of the complement system. By way of example, the use of in vitro ELISA (Enzyme-Linked Immunosorbent Assay) procedures to detect properdin associated with lipopolysaccharide (LPS) is a "simple, rapid and reliable method for the assessment of complement function particularly the detection of complement deficiency states". The authors conclude that the in vitro technique can be used in vivo with the same likelihood of success in detecting alternative complement pathway activation in disease states.

Similarly, the use of a blocking anti-properdin monoclonal antibody to study properdin binding with C3b using an in vitro hemolysis test was found to be an appropriate indication of both the role of properdin during infection and the mechanism of C3 convertase stabilization. Still further, the standard rabbit erythrocyte hemolysis assay (described in detail herein in Example 1), which assay is used to measure alternative complement pathway activity, is accepted in the art as being the "most convenient assay for the activity of the human alternative pathway".

We concluded from the data in FIG. 1 that Dextran Sulfate is an inhibitor of C5b-9 formation. We evaluated Dextran Sulfate effect in a cellular assay as a means of examining the effects of the Dextran Sulfate on alternative pathway function. Increasing amounts of the Dextran Sulfate were added to 10% human serum that was incubated with rabbit erythrocytes at 37° C. Using this erythrocyte lysis assay we determined that Dextran Sulfate at a concentration of 10 µg/ml caused inhibition of AP-dependent hemolysis of erythrocytes. Similar results were also obtained in hemolysis inhibition assays using rabbit and rat serum, (data not shown). Results from these cellular assays indicate that Dextran Sulfate is capable of full inhibition of AP function in human serum

EXAMPLE 7

NM3014 Inhibits Thrombin Formation in Citrated Normal Human Plasma

Citrated human plasma (100 µl) was mixed with various concentrations of Dextran Sulfate in the presence of constant concentration of S2238 (100 µl of 2 µg/ml). This mixture was treated with an optimized dose of innovin (aPTT reagent from Dade Behring, Innovin initiates a coagulation response. As a result thrombin is produced which reacts with S2238 to generate yellow color. S2238 reacts with thrombin as it is being produced. Dextran Sulfate at 10 µg/ml appears to have a partial effect on coagulation. Concentrations in the range of the data were recorded using Soft Max-Pro on Spectramax 190 kinetic spectramax.

EXAMPLE 8

NM3014 Inhibits Complement Activity in Rabbits with Antigen-Induced-Arthritis

Based on the data presented in Figure we administered 60 mg/Kg body weight to arthritic rabbits. Within ten minutes of Dextran Sulfate administration, complement activation was completely blocked compared to the vehicle-treated AIA rabbit values. However, when measurements were taken 24 hour later, we saw no inhibition of AP activity. Thus, while we were able to block AP activation at 60 mg/Kg this dose was not sufficient to inhibit AP activity of the 24-hour period between treatments. AP-complement activation was not inhibited in arthritic rabbits treated with the vehicle. These data indicate that Dextran Sulfate can reduce complement activation in vivo in rabbits with AIA, however, higher doses or increased frequency of dosing will be required to sustain the total inhibition of complement activation in the arthritic rabbits.

EXAMPLE 9

NM3014 Inhibits Cellular Infiltration into Knee Joints of Rabbits with Arthritis Synovial samples were also collected from the right and left knees of the AIA rabbits in this experiment and assessed for immunocyte infiltration 48-h after the last Dextran Sulfate or vehicle treatment. Dextran Sulfate treated rabbits had a significant decrease in the numbers of immunocytes that entered their arthritic knee joints (Per Ab-Ova bar) compared to arthritic knee joints (saline-Ova bar) of vehicle treated rabbits (FIG. 9). Data are presented as mean number of cells±SEM for each rabbit (N of 5 per treatment group, Stats: repeated measure ANOVA with Bonferoni Post-hoc test, *p<0.05). These findings indicate that Dextran Sulfate treatment prevents infiltration of immune cells, which direct and orchestrate inflammation and joint destruction, into the arthritic joint.

EXAMPLE 10

NM3014 Inhibits sC5b-9 in Normal Heparinized Whole Human Blood in Extra Corporeal Circulation (Tubing Loop) Model of Cardiopulmonary Bypass This study was conducted on heparinized Human Whole Blood from 10 different donors. Patients undergoing cardiopulmonary bypass (CPB) frequently manifest a generalized systemic inflammatory response syndrome. Clinically, these reactions are reflected in postoperative leukocytosis, fever, and extravascular fluid accumulation, which may lead to prolonged recovery and occasionally with serious organ dysfunction. The inflammatory responses consist of humoral and cellular changes that contribute to both tissue injury and impaired hemostasis. Complement activation has been implicated as the important cause of the systemic inflammatory reaction. Complement activation is attributed to the interaction between the blood and the surface of the extracorporeal circuit constituting CPB Primary inflammatory substances are generated after activation of the complement system, including the anaphylatoxins C3a and C5a, the opsonin C3b, and the membrane attack complex C5b-9. Both C3a and C5a has been shown to upregulate CD11b (integrin) and CD18 (integrin) of MAC-1 complex in polymorphonuclear cells PMN (comprising mainly neutrophils) in vitro and to induce lysosomal enzyme release by PMN. C5b-9 can induce the expression of P-selectin (CD62P) on platelets and both C5a and C5b-9 induce surface expression of P-selectin on endothelial cells. C3a and C5a stimulate chemotaxis of human mast cells and trigger the release of histamine which induces vascular permeability.

In vitro recirculation of whole blood in an extracorporeal bypass circuit has been used extensively as a model to simulate leukocytes and platelets changes and complement activation in CPB. The effectiveness of the Dextran Sulfate to inhibit the cellular and complement activation in human whole blood was studied using this extracorporeal circulation model for CPB.

Preparation of Tubing Loops: Tubing loops (PVC, cat # . . . VWR Scientific) were prepared by cutting a piece of polyvinyl tubing and connecting the ends of the tubing with a piece of silicone plug. Blood was drawn using 16 gauge needled from fasting healthy donors. The blood volume of 45 was drawn into a 50 ml polypropylene tube containing a final concentration of 5 units of heparin per ml of blood. The blood was diluted with 35 ml plasmalyte. The diluted blood (2 ml) was filled in each tubing loop. Duplicate tubing loops were prepared for each treatment. Blood samples were prepared as follows; no treatment, treated with various concentrations of Dextran Sulfate.

(2) Tubing Loop Operation and Sampling: The concentration of Dextran Sulfate was chosen based upon in vitro assay and the concentration of plasma. Concentrations of Dextran Sulfate in range of 800 µg/ml, 400 µg/ml, 200 µg/ml, 100 µg/ml, and 40 µg/ml. Prior to the addition of the untreated and treated blood to the extracorporeal circuit, a blood sample was taken from the stock of diluted blood and is designated baseline control. At that time, various concentrations of Dextran Sulfate in blood will be filled into the tubing loop. Following a 2 hours rotation at 37°, tubing loop samples were transferred to 2 ml polypropylene tubes and plasma samples were prepared by immediate centrifugation at 2,000 g. An aliquot of blood sample was removed for flow cytometry staining and analysis. A number of controls were put into place. From the donor we obtained serum, heparinized whole blood plasma, unrotated controls, rotated controls, and Dextran Sulfate treated samples.

EXAMPLE 10a

NM3014 Inhibits rRBC Hemolysis

Plasma aliquots for the alternative pathway hemolytic assays: Plasma samples were subjected to alternative pathway dependent hemolytic assay using AP buffer (GVB containing 10 mM magnesium chloride, 5 mM EGTA). Plasma concentrations were adjusted to 10% final in AP buffer. rRBC were incubated at 37° and the extent of hemolysis was obtained using kinetic run (SoftMax Pro, Molecular Devices, CA). The detailed method is given in example 1. As shown in FIG. 10a, complete inhibition of hemolysis is achieved with Dextran Sulfate at 800, 400, 200, and 100 µg/ml concentration of Dextran Sulfate. No inhibition of Dextran Sulfate activity was seen at the dose of around 40 µg/ml.

Plasma aliquots for measuring sC5b-9 in ELISA. Aliquots were appropriately diluted for the measurements of sC5b-9 complex in plasma. FIG. 10 shows that the production of sC5b-9 is completely inhibited by Dextran Sulfate in whole blood plasma following the tubing loop circulation. Dextran Sulfate at all doses up to 100 µg/ml inhibits complement activity as shown by the inhibition of sC5b-9 production. Inhibition of sC5b-9 is directly relevant to inhibition of the pathway.

The activation of neutrophils, monocyte and platelets were quantitated by measuring the levels of the cell-surface expression of CD11b and CD62P on neutrophils/monocytes and platelets, respectively. For CD11b labeling of neutrophils, 200 µl of whole blood collected from the circuits were immediately incubated with 20 µl of phycoerythrin (PE)-anti-CD11b antibody (Becton Dickinson, San Jose, Calif.) for 20 minutes at room temperature in a microcentrifuge tube. Then 2 ml of FACS Lysing Solution (Becton Dickinson) was added for 20 minutes at room temperature to lyse red blood cells and to fix leukocytes. The microcentrifuge tubes were centrifuged at 300 g for 5 minutes for leukocytes and 1200 g for platelets. The supernatant was aspirated and the cells resuspended in PBS for washing. The tubes were spun again, the supernatant aspirated, and the cells finally resuspended in 0.5 ml of 1% paraformaldehyde overnight prior to analysis using an BD-LSR flow cytometer (BD Biosciences). For double labeling to concomitantly identify the neutrophil population, 10 µl of fluorescein isothiocyanate (FITC)-anti-CD15 antibody (clone MMA, Becton Dickinson) were added for incubation together with PE-anti-CD11b antibody to stain neutrophils and anti-CD14 (FITC) along with PE-CD11b was used for monocytes.

EXAMPLE 10b

NM3014 Inhibits Neutrophil Activation and Example 10c: NM3014 Inhibits Monocyte Activation As shown in FIG. 10b, Dextran Sulfate inhibits neutrophil activation at a concentration range of 800 to 100 µg/ml. No inhibition was seen at 40 µg/ml. These studies are consistent with the results obtained for the inhibition of complement activity. These data demonstrate that inhibition of neutrophil CD11b expression is directly linked to inhibition of complement activity. Neutrophils bear both C3a and C5a receptors. Thus, prevention of C3a/C5a production should have direct effect on CD11b expression. Monocytes have been known to bear the C3a receptors. C3a produced because of complement activation is known to activate monocytes. Complement inhibitory agent Dextran Sulfate down regulates CD11b expression on monocytes as shown in FIG. 10c.

EXAMPLE 10d

Aspirin (COX Inhibitor) Inhibits NM3014 Induced Platelet Activation &

EXAMPLE 10e

GPIIb/IIIa (Antiplatelet Agent) Inhibits NM3014 Induced Platelet Activation

As shown in FIG. 10d, Dextran Sulfate activates platelets as shown by the increased CD62P staining in Dextran Sulfate treated samples compared to untreated controls. These results were puzzling based on role for platelets in hemostasis. All 12 donors demonstrated platelet activation above the control levels. The mechanism of how Dextran Sulfate activates platelets remains to be known. While platelets bear C3a receptors, it is not clear how platelets were being activated. In an effort to downregulate platelet activation, we performed an experiment in which Dextran Sulfate was utilized in combination with aspirin. Such a combination therapy not only prevented platelet activation above the control levels but also downregulated activation of platelets much below control levels. Similar results were obtained with a combination of Dextran Sulfate and GPIIb/IIIa an antibody known to bind GPIIb/IIIa receptors on platelets. These surprising results present Dextran Sulfate as a lead complement inhibitory drug that down regulates both complement and cellular activation in heparinized whole human blood. Shown in FIGS. 10$d$ and 10$e$ are results from this study.

For CD62P labeling of platelets, 100 µl of diluted blood collected from the circuits were immediately incubated with 20 µl of PE-anti-CD62P antibody (Becton Dickinson) for 20 minutes at room temperature in a polypropylene tube, Then the mixture was treated with FACS Lysing Solution as described above. The microcentrifuge tubes were centrifuged at 12000. g for 5 minutes. The platelets were washed in PBS/BSA 01%, fixed in 1% paraformaldehyde and then analyzed as described above. For double labeling to concomitantly identify the platelet population, 5 µl of FITC-anti-CD61 antibody were added for incubation together with PE-anti-CD62P antibody.

For flow cytometry measurement, the PMN (containing mainly neutrophils) and platelet populations were identified by live gating based on forward- versus side-scatter parameters and specific staining with FITC-anti-CD15 antibody and FITC-anti-CD61 antibody, respectively. The background staining was gated using isotype-matched labeled antibodies. The intensity of expression of CD11b and CD62P was represented by mean fluorescence intensity (MFI).

EXAMPLE 11

Dextran Sulfate 40,000 and 5,000 Molecular Weight Inhibits Joint Inflammation and Bone Destruction in Rat-AIA Lewis male rats were used to examine the effect of Dextran Sulfate combination with aggrastat (molecular weight 40,000 and 5,000) for the treatment of arthritis. Arthritis was induced in adult male Lewis rats (200-225 gm) by an intradermal injection of complete Freund's adjuvant (CFA) at the base of the tail on the dorsal side. The CFA (100 mg dried and heat killed *Mycobacterium butyricum* (Difco, Detroit, Mich.) emulsified in 10 ml sterile mineral oil) was prepared by grinding the bacteria powder with a mortar and pestle until the bacterial cell wall turned from a light beige to an eggshell white powder. The mineral oil was then slowly mixed into the bacterial cell wall using the mortar and pestle. All animals in each experiment were challenged with the same preparation of adjuvant and nearly 100% of the animals developed arthritis. Dextran Sulfate was obtained from Sigma Aldrich Corp and Aggrastat was purchased from the pharmacy. Dextran Sulfate was dissolved in aggrastat. The drug treatment started on day 10 post-immunization, the time of disease onset, and continued until sacrifice. The dose of Dextran Sulfate was 20 & 10 mg/Kg/per day per 150-200 g rat. The inflammatory response was assesed by the measurement of paw volume. Paw volume appears to be very consistent and gave slow increasing arthritis over time. Paw volumes were measured every day until sacrifice using Plethysmometer (IITC). After the sacrifice/euthanasia, limbs were removed and processed for;

a) histological evaluations: Only three animals were used per group. Sections were stained with Eosin and hematoxylin to identify various regions within the inflamed limb. Untreated controls have intact cartilage layer and the bone (Score 0) and clear synovium without pannus. Arthritic controls had no defined cartilage bone, and have pannus layer and significant inflammation (Score 5). Enbrel was used as positive control. The histological assessment suggests that there is less cartilage degradation and nearly no pannus visible. We gave a score of 2. All Dextran Sulfate (with aggrastat) treated samples also received a score of 2 because histological assessment appeared to be comparable.

b) Paw Swelling: Each paw was measured for water displacement using plethysmometer. Paw volume was measured every day. Dextran Sulfate 40,000 molecular weight (with Aggrastat) significantly decreased the paw swelling compared to untreated controls. Dextran Sulfate 5,000 (added with aggrastat) also decreased the inflammation.

Continuous treatment of Dextran Sulfate therapies from disease onset affected paw swelling in arthritic rats. All adjuvant-challenged rats developed AA between days 10-12. Soft tissue swelling was significantly decreased in Dextran Sulfate -treated animals compared with the vehicle-treated AA rats by day 28 post-adjuvant injection combination treatment Dextran Sulfate +aggrastat treatment significantly reduced the soft tissue swelling in the hind limbs, an effect which was maintained through day 28 compared with the vehicle-treated arthritic rat. While inflammation was decreased in these treatment groups, we observed a greater effect for these drugs in prevention of bone and cartilage destruction. Histological analysis of the ankle joints revealed that vehicle-treated arthritic rats had visible soft tissue swelling, bone loss, periosteal bone formation, narrowing of their joint spaces, and a decreased bone density by day 28. Dextran and aggrastat combination resulted in an about 60% decrease in paw inflammation compared to vehicle-treated AA rats.

Having described the invention, the following is claimed:

1. A method of treating arthritis in a subject in need thereof comprising: administering to the subject an amount of Dextran Sulfate effective to inhibit alternative pathway-dependent complement activation in the subject and an amount of an antiplatelet agent effective to inhibit platelet activation and/or platelet aggregation in the subject, wherein the antiplatelet agent comprises a GPIIb/IIIa receptor antagonist or GPIIb/IIIa inhibitor.

2. The method of claim 1, wherein the Dextran Sulfate has a molecular weight of about 1000 Da to about 500,000 Da.

3. The method of claim 2 wherein the Dextran Sulfate is administered to the subject at an amount effective to inhibit at least one of: formation of MAC, formation of alternative pathway derived C3a, C3b, and C5a, activation of immune cells, neutrophils, and monocytes, or formation of thrombin.

4. The method of claim 1, wherein the GPIIb/IIIa receptor antagonist or GPIIb/IIIa inhibitor comprises at least one of aggrastat, ticlopidine, or eptifibatide.

* * * * *